United States Patent
Raffy et al.

(10) Patent No.: US 10,226,299 B2
(45) Date of Patent: *Mar. 12, 2019

(54) TREATMENT OUTCOME PREDICTION FOR LUNG VOLUME REDUCTION PROCEDURES

(71) Applicant: Vida Diagnostics, Inc., Coralville, IA (US)

(72) Inventors: Philippe Raffy, Edina, MN (US); Youbing Yin, Coralville, IA (US)

(73) Assignee: Vida Diagnostics, Inc., Coralville, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/362,343

(22) Filed: Nov. 28, 2016

(65) Prior Publication Data

US 2017/0143428 A1 May 25, 2017

Related U.S. Application Data

(63) Continuation of application No. 14/188,005, filed on Feb. 24, 2014, now Pat. No. 9,504,529.

(51) Int. Cl.
*A61B 5/05* (2006.01)
*A61B 34/10* (2016.01)
(Continued)

(52) U.S. Cl.
CPC ............ *A61B 34/10* (2016.02); *A61B 5/7246* (2013.01); *A61B 5/7275* (2013.01);
(Continued)

(58) Field of Classification Search
CPC ... A61B 34/10; A61B 90/37; A61B 17/00234; A61B 6/5217; A61B 5/7275;
(Continued)

(56) References Cited

U.S. PATENT DOCUMENTS 7,611,452 B2  11/2009  Allison et al.
9,076,201 B1   7/2015  Negahdar et al.
(Continued)

FOREIGN PATENT DOCUMENTS

CN      1395713 A     2/2003
WO   2005007023 A2    1/2005

OTHER PUBLICATIONS

Cetti, E.J. et al., "Collateral ventilation," Thorax Journal, vol. 61, 2006, pp. 371-373.
(Continued)

*Primary Examiner* — Sanjay Cattungal
(74) *Attorney, Agent, or Firm* — Fredrikson & Byron, P.A.

(57) ABSTRACT

Systems and methods for displaying a predicted outcome of a lung volume reduction procedure for a patient including a user interface, a processor, and programing operable on the processor for displaying a predicted outcome of the bronchoscopic lung volume reduction procedure on the user interface, wherein displaying the predicted outcome of the lung volume reduction procedure includes receiving patient data comprising volumetric images of the patient, analyzing the volumetric images to identify one or more features correlated to treatment outcome prediction, predicting an outcome for a treatment modality or treatment device using the one or more identified features, and displaying the predicted outcome on the user interface.

20 Claims, 15 Drawing Sheets

(51) Int. Cl.
  *A61B 5/00* (2006.01)
  *A61B 6/00* (2006.01)
  *A61B 17/00* (2006.01)
  *G06F 19/00* (2018.01)
  *A61B 90/00* (2016.01)
  *G16H 50/20* (2018.01)
  *G06N 5/04* (2006.01)

(52) U.S. Cl.
  CPC ...... *A61B 6/5217* (2013.01); *A61B 17/00234* (2013.01); *A61B 90/37* (2016.02); *G06F 19/00* (2013.01); *G06F 19/30* (2013.01); *G06F 19/3418* (2013.01); *G06N 5/04* (2013.01); *G16H 50/20* (2018.01); *A61B 2017/00809* (2013.01); *A61B 2034/104* (2016.02); *A61B 2034/105* (2016.02)

(58) Field of Classification Search
  CPC ............ A61B 5/7246; A61B 2034/104; A61B 2034/105; A61B 2017/00809; G06F 19/3418; G06F 19/00; G06F 19/30; G16H 50/20; G06N 5/04
  USPC .................................................. 600/473–480
  See application file for complete search history.

(56) References Cited

U.S. PATENT DOCUMENTS

| | | |
|---|---|---|
| 2003/0051733 A1 | 3/2003 | Kotmel et al. |
| 2007/0092864 A1 | 4/2007 | Reinhardt et al. |
| 2010/0305463 A1 | 12/2010 | Macklem et al. |
| 2011/0071404 A1 | 3/2011 | Schmitt et al. |
| 2012/0249546 A1 | 10/2012 | Tschirren et al. |
| 2012/0284657 A1 | 11/2012 | Hafey et al. |
| 2014/0105472 A1 | 4/2014 | Yin et al. |
| 2014/0275952 A1 | 9/2014 | Monroe et al. |

OTHER PUBLICATIONS

Herth, F.J.F. et al., "Radiological and clinical outcomes of using Chartis™ to plan endobronchial valve treatment.," European Respiratory Journal, electronic publication May 3, 2012, retrieved from http://erj.ersjournals.com/content/41/2/302 on Sep. 30, 2014.

Mishima, M. et al., "Complexity of terminal airspace geometry assessed by lung computed tomography in normal subjects and patients with chronic obstructive pulmonary disease," Proceedings of the National Academy of Sciences, vol. 96, No. 16, Aug. 3, 1999, pp. 8829-8834. Abstract only.

The National Lung Screening Trial Research Team, "Reduced Lung-Cancer MOrtality with Low-Dose Computed Tomographic Screening," The New England Journal of Medicine, vol. 365, No. 5, Aug. 4, 2011, pp. 395-409.

Obuchowski, N.A., "ROC Analysis," American Journal of Roentgenology, vol. 184, Feb. 2005, pp. 364-372.

Sciurba, F.C. et al., "A Randomized Study of Endobronchial Valves for Advanced Emphysema," The New England Journal of Medicine, vol. 363, No. 13, Sep. 23, 2010, pp. 1233-1244.

Venuta, F. et al., "Long-term follow-up after bronchoscopic lung volume reduction in patients with emphysema," European Respiratory Journal, vol. 39, No. 5, 2012, pp. 1084-1089.

Witten, I.H. et al., "Data Mining: Practical Machine Learning Tools and Techniques," Morgan Kaufmann Publishers, Burlington, MA, 2011, Third Edition.

Yuan, R. et al., "Quantification of lung surface area using computed tomography," Respiratory Research, vol. 11, No. 153, 2010, 9 pages.

Zach, J. et al., "Correlations of CT Low Attenuation Cluster Size with Visually Assessed Extent and Pattern of Emphysema," ATS, 2013, 1 page.

Monroe, William S. et al., U.S. Appl. No. 61/782,308, "Treatment Planning for Lung Volume Reduction Procedures," filed Mar. 13, 2014, 36 pages.

Brown, et al., "CAD in clinical trials: Current role and architectural requirements," Available online at www.sciencedirect.com, Apr. 20, 2007, 6 pages.

Reymond, et al., "Prediction of Lobar Collateral Ventilation in 25 Patients With Severe Emphysema by Fissure Analysis With CT," Cardiopulmonary Imaging—Original Research, Oct. 1, 2013, 6 pages.

Yukitaka et al., "A study on quantifying COPD severity by combining pulmonary function tests and CT image analysis," Medical Imaging 2011: Computer-Aided Diagnosis, Mar. 3, 2011, 9 pages.

Communication Relating to the Results of the Partial International Search for International Application No. PCT/US2015/017077, 3 pages, dated May 6, 2015.

Herth et al., "Efficacy Predictors of Lung Volume Reduction with Zephyr Valves in a European Cohort," European Respiratory Journal, vol. 39, No. 6, Jan. 26, 2012, pp. 1334-1342.

U.S. Appl. No. 61/712,700, entitled "Visualization and Characterization of Pulmonary Lobar Fissures," filed Oct. 11, 2012, 18 pages.

"InterVapor—How it Works," Uptake Medical, Retrieved online from <https://web.archive.org/web/20121124070645/http://www.uptakemedical.com/about-intervapor/how-it-works, dated Nov. 24, 2012, 3 pages.

Austin, "Pulmonary emphysema: imaging assessment of lung volume reduction surgery," Radiology, vol. 212, No. 1, Jul. 1999, pp. 1-3.

TREATMENT OUTCOME PREDICTION FOR LUNG VOLUME REDUCTION PROCEDURES

CROSS-REFERENCES

This application is a continuation of U.S. application Ser. No. 14/188,005, filed Feb. 24, 2014, the contents of which are hereby incorporated by reference in its respective entirety.

BACKGROUND OF THE INVENTION

Severe emphysema is a debilitating disease that limits quality of life of patients and represents an end state of Chronic Obstructive Pulmonary Disease (COPD). It is believed that 3.5 million people in the US have the severe emphysematous form of COPD, and it is increasing in both prevalence and mortality. Current treatment methods for severe emphysema include lung volume reduction (LVR) surgery, which is highly invasive, and can be risky and uncomfortable for the patient. New treatment methods for treating emphysema include bronchoscopy guided lung volume reduction devices that aim to close off ventilation to the diseased regions of the lung, but maintain ventilation to healthier lung. Bronchoscopy-guided techniques have the promise to be less invasive, less costly and more highly accurate treatments for patients with severe disease and improve the quality of life of severe emphysema patients.

Emphysema can present itself in various disease forms (i.e., phenotypes). Predicting the right treatment for these patients at the appropriate time in the disease process may depend on the phenotype of the disease. Imaging techniques provide an in-vivo mechanism to objectively quantify and characterize disease phenotype and can be used as the patient selection process for the various procedural options. Quantitative imaging biomarkers can be used to effectively phenotype disease and therefore predict those patients most likely to respond to the targeted treatment options. By triaging the right patient to the appropriate therapy, there exists a greater promise for a positive impact on patient outcome, reduced healthcare costs, and replacing more invasive procedures like LVR surgery in treating patients with severe emphysema.

Bronchoscopic procedures such as the placement of pulmonary valves, coils, and the use of bio-sealants and energy delivery for lung volume reduction can provide effective ways of treating emphysema by shrinking over-inflated portions of the lungs. However, because of the complexity of lung anatomy and the diversity of disease among individuals, planning for such procedures can be difficult. For example, it can be difficult to determine which locations are best suited for the placement of valves and whether how such locations can be best accessed bronchoscopically. Difficulties can therefore arise after such a treatment is already in progress, such as difficulties in accessing the location for placement of the valve or delivery of the bio-sealant or energy, or the results of such treatment may be less effective than anticipated due to disease aspects that might not have been appreciated before the procedures such as fissure integrity and the presence of collateral ventilation.

Another lung disease, lung cancer, is the world's leading cause of cancer death, causing more annual deaths (about 28% of all cancer deaths) than any other cancers for which there are routing screening programs such as breast, colorectal, and prostate. Lung cancer comprises about 14% of cancer diagnoses each year, including smokers as well as non-smokers. Only about 15% of lung cancer cases are diagnosed at an early stage while 85% are diagnoses at a late stage. As with all cancers, early detection of lung cancer is critical to patient outcome. However, the five-year survival rate for lung cancer is only about 16%, and over half of patients die within the first year of diagnosis. The five-year survival rate for lung cancer is much lower than that of many other leading cancers, but this could be improved through improved early detection.

One method of screening for lung cancer uses low-dose computed tomography (CT), which resulted in a 20% reduction in lung cancer mortality in one trail. The U.S. Preventive Services Task Force has recommended annual screening for lung cancer using low-dose CT for adults aged 55 to 80 years old who have a 30 pack-year smoking history and currently smoke or have quit within the past 15 years, due to the increased risk for lung cancer in this population. However, several publications have shown an association between radiographic emphysema and airflow obstruction and lung cancer, confirming the presence of emphysema or airflow obstruction in most middle-aged to older long-term smokers and ex-smokers with proven lung cancer. Therefore, while the criteria currently employed for selecting patients for low-dose CT lung cancer screening are useful, other factors may also be useful and a more refined selection process could make lung cancer screening more cost effective.

SUMMARY

Certain embodiments of the present invention are described in the following illustrative embodiments. Various embodiments include systems and methods for planning lung procedures such as lung volume reduction procedures using predictions based on volumetric patient lung images. Other various embodiments include systems and methods for predicting lung cancer risk and for recommending screening regimens for patients using predictions based on volumetric images of the patient's lungs.

In some embodiment, a system for displaying a predicted outcome of a lung volume reduction procedure for a patient includes a user interface, a processor, and programing operable on the processor for displaying a predicted outcome of the bronchoscopic lung volume reduction procedure on the user interface. Displaying the predicted outcome of the lung volume reduction procedure may include receiving patient data including volumetric images of the patient, analyzing the volumetric images to identify one or more features correlated to treatment outcome prediction, predicting an outcome for a treatment modality or treatment device using the one or more identified features, and displaying the predicted outcome on the user interface.

The system may further include receiving a selected treatment location within the airway tree from a user and predicting an outcome for a treatment modality or treatment device at the selected location using the one or more identified features. In some embodiments, displaying the predicted outcome of the lung volume reduction procedure further includes receiving a selected treatment modality from the user, and predicting an outcome for a treatment modality includes predicting an outcome for the treatment modality selected by the user.

In some embodiments, predicting an outcome for a treatment modality includes predicting a plurality of outcomes for a plurality of treatment modalities, and displaying the predicted outcome on the user interface includes displaying the plurality of treatment outcomes for the plurality of treatment modalities on the user interface.

In some embodiments, the system further includes programming operable on the processor for analyzing the volumetric images to identify lobes, sublobes and an airway tree of the lungs and displaying a three dimensional model of the patient's lungs on the display.

In some embodiments, the predicted outcome may be a numerical value representing a probability of success. In some such embodiments, success may be a lung volume reduction greater than a threshold value. In some embodiments, the predicted outcome includes a numerical value representing a probability of pneumothorax. In some embodiments, the predicted outcome includes a first numerical value representing a probability of lung volume reduction greater than a threshold value and a second numerical value representing a probability of pneumothorax.

In some embodiments, analyzing the volumetric images to identify one or more features correlated to treatment outcome prediction comprises measuring low attenuation clusters. In some embodiments, the one or more features include a feature corresponding to fissure integrity. In some embodiments, analyzing the volumetric images to identify one or more features correlated to treatment outcome prediction comprises measuring peripheral vessel volume.

Other embodiments include a system for displaying an outcome of a lung volume reduction procedure for a patient including a user interface, a processor, and programming operable on the processor for displaying a predicted outcome of the bronchoscopic lung volume reduction procedure on a user interface. Displaying the predicted outcome of the lung volume reduction procedure includes receiving patient data comprising volumetric images of the patient, analyzing the volumetric images to identify lobes and airway tree of the lungs, analyzing the volumetric images to identify one or more features correlated to treatment outcome prediction, displaying a three dimensional model of the patient's lungs, receiving a selected treatment location within the airway tree from a user, predicting an outcome for a treatment modality or treatment device at the selected location using the one or more identified features, and displaying the predicted outcome on the user interface. Displaying the predicted outcome of the lung volume reduction procedure may further include receiving a selected treatment modality or treatment device from the user, and predicting an outcome for a treatment modality may include predicting an outcome for the treatment modality or treatment device selected by the user. In some embodiments, displaying the predicted outcome of the lung volume reduction procedure further includes displaying a probability of a successful treatment outcome and a probability of an adverse event for a plurality of lung volume reduction treatment modalities and receiving a selection of a treatment modality from a user.

In some embodiments, predicting an outcome for a treatment modality or treatment device includes predicting a plurality of outcomes for a plurality of treatment modalities or treatment devices, and displaying the predicted outcome on the user interface includes displaying the plurality of treatment outcomes for the plurality of treatment modalities on the user interface.

In some embodiments, the predicted outcome includes a numerical value representing a probability, such as a probability of success.

In some embodiments, predicting an outcome for the selected treatment modality using one or more identified features includes comparing the one or more features identified in the patient lungs to a database to predict an outcome of treatment at the selected location with the selected treatment modality. The database may include a set of outcomes for lung volume reduction procedures for a group of individuals using the selected treatment modality and further may include a set of volumetric images or one or more features identified in the volumetric images for the group of individuals, and the identified features in the volumetric images of the group of individuals may be the same features as the identified features in the volumetric images of the patient.

Other embodiments include a method of planning a lung volume reduction procedure for a patient using a treatment planning and outcome system, the system comprising a processor and a user interface. The method includes observing a three dimensional model of the patient's lungs on the user interface generated by the processor using patient data comprising volumetric images, selecting a treatment modality, selecting a treatment location, and observing a predicted outcome on the user interface. The predicted outcome may be generated by the using outcome predictors determined using the patient data. The method may further include observing a predicted outcome for a plurality of treatment modalities generated by the processor and displayed on the user interface prior to selecting a treatment modality.

Still other embodiments include systems for selecting patients for lung cancer screening comprising. In some such embodiments, the system includes a user interface, a processor, and programing operable on the processor for displaying a lung cancer risk or a recommendation for lung cancer screening. Displaying the lung cancer risk or the recommendation for lung cancer screening includes receiving patient data comprising volumetric images of the patient, analyzing the volumetric images to identify one or more features correlated to lung cancer, predicting a likelihood of lung cancer using the one or more identified features, and displaying the predicted likelihood of lung cancer on the user interface or displaying the recommendation for lung cancer screening. The recommendation for lung cancer screening may be determined by the system using the predicted likelihood of lung cancer.

BRIEF DESCRIPTION OF THE DRAWINGS

The following drawings are illustrative of particular embodiments of the invention and therefore do not limit the scope of the invention. The drawings are not necessarily to scale (unless so stated) and are intended for use with the explanations in the following detailed description.

Embodiments of the invention will hereinafter be described with the appended drawings, wherein like numerals denote like elements.

DETAILED DESCRIPTION

Figure 1:
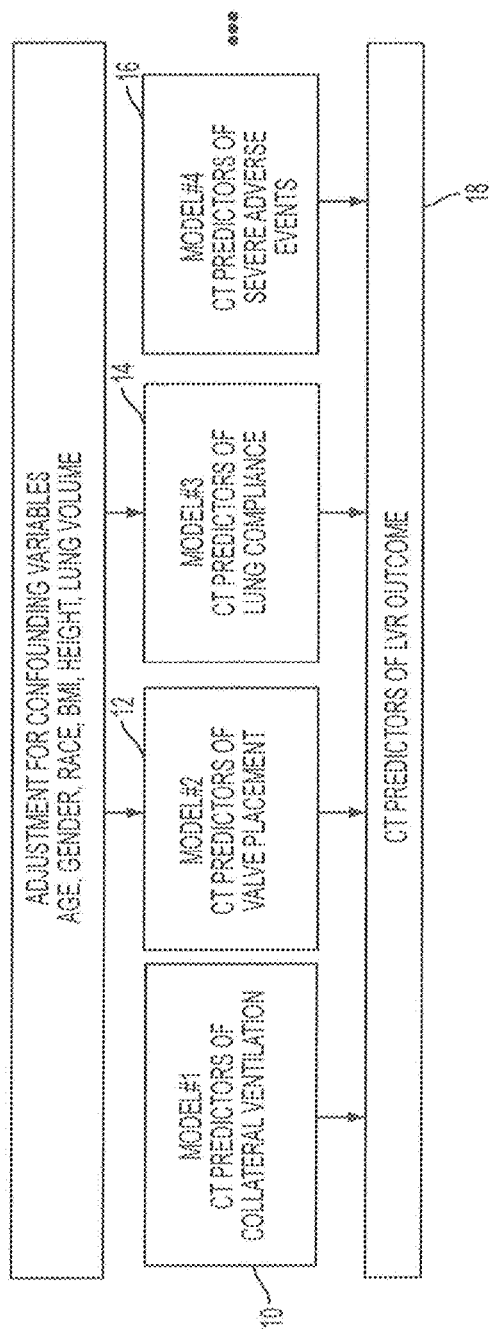
FIG. 1 is an example of a schema for prediction of an outcome of a lung volume reduction procedure.

Embodiments described herein include systems for predicting various aspects of lung diseases, including form, stage, or severity. Some embodiments predict the outcome for one or more procedures, such as the outcome of a lung volume reduction procedure for the pulmonary diseases such as emphysema. Because of the complexity of the lungs and anatomical differences amongst individuals, a wide variety of factors can influence disease form and severity and the success of interventional pulmonary procedures. Various embodiments can identify predictors and can predict the outcome of procedures such as interventional pulmonary procedures and may be used as a part of treatment planning for interventional pulmonary treatments such as lung volume reduction treatments, including valve placement, the use of bioadhesives and energy modalities. The treatment outcome prediction system may provide a clinician with enhanced visualization and analysis of the lungs including assisting the clinician with triaging patients and with planning a procedure with the highest likelihood of a successful outcome.

Various embodiments predict the outcome of an interventional pulmonary procedure using measurements obtained from patient images and/or other patient data. The patient images may be patient images or imaging data produced by CT scans, MM scans, and/or PET scans or other volumetric images, for example. The measurements may be predictors that may be used individually or in combination to identify a person's disease form, stage, and/or severity and/or to predict a person's outcome from a procedure. Measurements which may be used as predictors include quantitative measurements of the lung parenchyma and/or airways. For example, density, texture, airway morphology (such as diameter, cross-sectional area, length, tapering, wall thickness, and/or wall area of a particular airway), pulmonary vessels (such as size, size relative to neighboring airway, volume of peripheral vessels relative to total volume of pulmonary vasculature), fissure characterization, or functional measurements such as measurements of air trapping (determined either from the patient images or from a separate measurement). Fissure characterization may be determined as described in U.S. patent application Ser. No. 13/804,542, for example, the disclosure of which is incorporated herein by reference.

In some embodiments, the predictors may be identified using a training database. The training database may include information from a large group of individuals. The information may include the patients' personal characteristics such as age, gender, race, body mass index, height, and/or lung volume, among other things which may be considered confounding variables and which may be used to categorize the patients within the database for refining the information contained in the database. The information in the database may also include imaging data including the imaging data itself and/or data obtained by analysis of the images or imaging data, such as measurement of various anatomical features determined using the imaging data, such as the predictors described above. The information may further include information relating to patient treatment and outcome, including type of treatment such as type of lung volume reduction procedure, location of treatment within the lung, the results of treatment, pulmonary function tests, amount of lung volume reduction, performance test results such as 6 minute walk distance, and occurrence of adverse events following the procedure, such as pneumothorax or death. The type of lung volume reduction procedure may include valve placement, energy delivery, or biosealant, for example. The device information may further include the type of device, the type of valve (such as endobronchial or intrabronchial) and the specific manufacturer and/or model of the device. The information in the database may further include information from other studies besides the volumetric images, such as results of direct measurements such as testing for collateral ventilation, which may be performed using the Chartis System from Pulmonx, for example. The information may further include results from pulmonary function studies (such as FEV1, FEV1/FVC, and FEF) and patient questionnaires (such as the Saint George's Respiratory Questionnaire (SGRQ) and the Modified Medical Research Council Dyspnea Scale (mMRC)), for example. The training database is sufficiently large that statistically significant associations can be identified, such as associations between measurements of anatomical features and results of lung volume reduction procedures, which can be used as predictors. In some cases, the predictors may be identified for each subgroup of individuals, such as individuals of a particular age, gender, race, body mass index, height, lung volume and/or valve type or procedure type.

Predictors of patient disease state (such as form of disease, stage, or severity) and/or of treatment outcomes may be derived from the training database, such as by extraction from multiple regression analysis. For example, correlations between one or more measurements of anatomical features using patient images and outcomes of lung volume reduction procedures may be identified in the training database, and the measurements may be used as a predictor in evaluating patients who are not included in the training database for clinical decision making. The predictors may be identified and used for triaging patients into those for whom a procedure is recommended versus those for whom the procedure is not recommended, and may be used for outcome prediction.

The patient predictors may be used singly to predict a disease state and/or an outcome. Alternatively, two or more predictors may be used in combination to predict a disease state and/or an outcome for a patient. In some embodiments, multiple predictors may be used to create a classification schema. A patient's data, such as the patient's lung images, may be analyzed to classify them with regard to the multiple predictors used in the classification scheme and a prediction of the outcome may be obtained based on the classification schema.

The outcomes identified using the training database and/or predicted for individual patients according to various embodiments may include the success of the procedure such as a lung volume reduction procedure. A procedure may be classified as successful if certain criteria are met, as discussed further below.

The predictors may be one or more key measurements predictive of a treatment response. The predictors may be used in combination using an existing classification schema. Alternatively, several types of supervised classifiers may be used ranging from simple rule based classifiers to tree-based classifiers, Naïve Bayes Classifier, random forest algorithm, or more sophisticated classifiers which may use a combination of models as described in the machine learning literature, for example. The classification steps may result in an ROC analysis that indicates the sensitivity, specificity, and positive and negative predictive value of the test for predicting a result, such as for predicting a positive outcome for LVR treatment.

Once a predictor or set of predictors has been identified using the training database, the predictor or predictors can be applied for use with patients. As such, the training database may be used to identify predictors, and then the predictor or predictors can be used by a system to predict disease state and/or treatment outcome, for example, as described further below. The training database may be updated from time to time with additional data, and/or additional features may be identified in the data, after which the predictors may be updated to refine their predictive abilities. Such updated predictors may then be transmitted to the system for predicting patient disease state and/or treatment outcome.

A positive outcome may be identified by meeting one or more objective criteria, which may be measurements, such as measurements which can be obtained from a patient volumetric image such as a CT. For example, a positive treatment response may be identified by a lung volume reduction in the treated lung of at least a selected threshold value, such as 350 cubic centimeters. Alternatively, the percentage of lung volume reduction of the treated lobe may be used to determine whether the threshold value of successful lung volume reduction has been achieved. In another alternative, the increase in the FEV1 after treatment may be used to determine whether the procedure was successful. For example, a cut off value of at least a 12% increase in FEV1 may be used as indicating a successful treatment outcome. In some embodiments, an improvement in carbon monoxide diffusing capacity (DLCO) may be used to determine whether a procedure was successful. In some embodiments, the subjective improvement in symptoms may be used to determine whether a procedure was successful. For example, the improvement in the quality of life may be determined using a standard test such as the St. George's Respiratory Questionnaire (SGRQ), and a particular numerical or percentage increase may be used as a threshold to indicate success of a procedure. The threshold values for any measurement of success may be preset in the system or may be selected by a clinician using a treatment planning and outcome prediction system, for example. In some embodiments, the occurrence of certain adverse event may override any findings indicative of success. Such adverse events may include death, pneumothorax, and/or movement of an implanted device for example. If such adverse events occur, the patient outcome may be categorized as not a success, even if the threshold values are met.

In some embodiments, the system may predict the likelihood of an adverse event. Adverse events may include the occurrence of pneumothorax, such as pneumothorax in the treated lung within a threshold period of time following the treatment, or death of the patient within a threshold period of time following the treatment. The thresholds may be selected such that the adverse event is likely to be causally related to the procedure. Other events that may be considered adverse include movement of an implanted device such as a one way valve, such as movement into a child branch or bifurcation after implantation.

In still other embodiments, the predictors may be used to identify one or more features of the patient's lung images, which may in turn be used to predict treatment outcome. One such feature, which may be identified in the patient's lung images is the presence of collateral ventilation, which may or may not be used, in turn, to predict treatment outcome. For example, one or more anatomical features, which may be identified in the patient images may be correlated to the presence of collateral ventilation using the training database. These anatomical features may then be used as predictors to predict the presence of collateral ventilation in a patient. Furthermore, the presence of collateral ventilation as directly measured, such as using the Chartis Pulmonary Assessment System™, or as predicted using the image based predictors, may further be correlated to outcomes, such as successful treatment or occurrence of an adverse event, and may therefore be used to predict patient outcomes.

In some embodiments, the predictors identified using the training database may be separately determined for distinct patient populations within the training database based on one or more personal characteristics of the patients (such as age, gender, race, BMI, height, and lung volume). The prediction model applied to a patient may be based upon a matching patient population within the training database having the same personal characteristics. In this way, the confounding effects of the personal characteristics on outcome prediction can be eliminated, making the patient prediction process more powerful (more sensitive and specific).

In some embodiments, the development of a predictive model may first include determining a predictive model including one or more predictive parameters using a large training database of patients and outcomes for a particular treatment, and then applying the predictive model to an independent test database to predict treatment outcome. The individuals included in the training databases may be selected to include a similar patient population and/or similar procedure type as those in the test population. The test database may then be analyzed to determine whether the predictions were correct.

Some embodiments may be used for predicting the outcome of a procedure, such as a lung volume reduction procedure. The lung volume reduction procedure may be an endoscopic procedure such as placement of a one-way valve, coil, biosealant delivery, or heat energy delivery. Alternatively, embodiments may be used to predict other pulmonary treatment outcomes or aspects of pulmonary disease such as the disease form, stage or severity or severity of COPD, emphysema (e.g., centrilobular, panlobular, paraseptal), asthma, lung cancer, or other pulmonary diseases. The training database used for identifying such predictors would include data identifying these other treatment outcomes or aspects of disease, which may have been determined by conventional means such as radiological studies, physical examination, pathological examination of tissue samples, or other methods.

In some embodiments, various predictors may be used in combination to predict patient status for various conditions or features, and the predicted conditions or features may be used in combination to predict patient outcome or disease status. An example of such a combination of predictions to predict treatment outcome is shown in FIG. 1. In this example, a first model 10 is used to predict collateral ventilation, a second model 12 is used to predict valve misplacement, which may be based upon characteristics of the airway into which the valve would be placed and the nature of the surrounding tissue, a third model 14 is used to predict lung compliance, and a fourth model 16 is used to predict adverse events. In each of these models, the prediction of each condition or feature may be made based upon features in the patient's volumetric images such as CT scans, though other radiologic scans could alternatively be used. The results of one or more or all four of the models may then be used to predict the response to treatment 18, such as to lung volume reduction treatment. Each of the models, and the final treatment outcome prediction, may be adjusted for patient characteristics such as age, gender, race, BMI, height, and lung volume, which could otherwise confound the predictions. One or more of the predictions made by each of these models and the final treatment outcome prediction may be made automatically and presented to a clinician to assist with patient selection as part of a treatment planning and prediction system.

The results that are presented to the clinician may be a prediction that one or more features are either present or absent, such as that collateral ventilation is present or absent in a particular lobe or sub-lobe. Alternatively or additionally, the results may be presented as a predicted likelihood, such as a likelihood that a feature is present or that an outcome will occur, such as a likelihood that collateral ventilation is present (such as in an amount above a particular threshold), which may be presented as a percentage or other numerical value representing likelihood.

Figure 2:
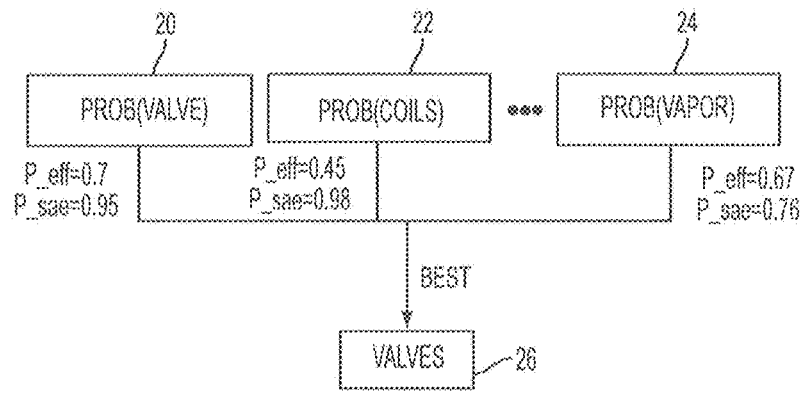
FIG. 2 is an example of outcome prediction for various treatment modalities and identification of a preferred treatment modality.

In some embodiments, the predictors may be used to assist a clinician in selection of a treatment modality. For example, each treatment modality, such as valve placement, coil placement, bio-sealant delivery, energy delivery, stents, etc., may have a different predicted efficacy and safety (risk of adverse events) associated with its use in a particular patient. Embodiments of the invention may therefore determine the likelihood of a successful outcome and/or the likelihood of an adverse event for a particular patient using one or more predictors, and may present this information to a clinician, and may even present a preferred treatment modality. The clinician may use this information when selecting a treatment modality. A representation of such a system for device selection is shown in FIG. 2. The probabilities may be separately determined for each type of treatment modality, in this case valve placement 20, coil placement 22, and energy delivery (vapor) 24, though other or additional modalities may also be used. The likelihood of a successful result (indicated as P_eff) and of a severe adverse events (indicated as P_sae) are determined for each modality and may be displayed for a clinician. The valve is selected as the best option at 26.

The outcome predictors may be used in conjunction with treatment planning, such as in conjunction with, or as a component of, a lung volume reduction treatment planning system. In such cases, the system may be a treatment outcome prediction system. The treatment outcome prediction system may utilize volumetric images or imaging data to analyze and identify patient anatomy and may further present 3 dimensional models of the patient pulmonary anatomy to a clinician.

The treatment outcome prediction system may include a processor, such as a processor in a computer, and may also include a visual display such as a monitor or other display screen. The system may also include instructions included in software, stored in memory of the system, and operable on the processor. The software may include instructions for the processor to perform the various steps and methods described herein, including instructions to receive patient data including volumetric imaging data, analyze the data, display images including three-dimensional images of the pulmonary tree, receive physician input, and analyze the pulmonary anatomy in light of the clinician input, and supply information to the clinician, and suggest treatment locations and approaches. In some embodiments, the treatment outcome prediction software may be incorporated into 3D pulmonary imaging software. In some embodiments, the treatment outcome prediction software and the 3D pulmonary imaging software may be separate software but may each be implemented by and/or incorporated into a common system. An example of 3D pulmonary imaging software that may be used in combination with the treatment planning software is the APOLLO quantitative pulmonary imaging system software available from VIDA Diagnostics, Inc.

Embodiments of the invention may allow the clinician to interact with the three-dimensional model of the lungs and the two-dimensional volumetric images associated with the 3-dimensional model. For example, the three-dimensional model and the associated two-dimensional images may be presented in a graphical user interface on a visual display. The user may interact with the graphical user interface, such as by selecting a button, icon, and/or one or more locations on the images or the model or elsewhere using a mouse, stylus, keypad, touchscreen or other type of interface known to those of skill in the art. The creation of the three-dimensional model may be performed by the system including a processor with software instructions to perform this function as well as software to permit a user to interact with the graphical user interface, to calculate and display desired data and images, and to perform the other functions described herein. The system may further include the visual display on which the graphical user interface is displayed. The three-dimensional model and two-dimensional images may be provided to a user (such as a clinician or researcher) as a graphical user interface on a visual display, which may be a computer screen, on which the images and data may be manipulated by the user. Outcome predictions may also be provided on the visual display.

Examples of the embodiments may be implemented using a combination of hardware, firmware, and/or software. For example, in many cases some or all of the functionality may be implemented in executable software instructions capable of being carried out on a programmable computer processor. Likewise, some examples of the invention include a computer-readable storage device on which such executable software instructions are stored. In certain examples, the system processor itself may contain instructions to perform one or more tasks. System processing capabilities are not limited to any specific configuration and those skilled in the art will appreciate that the teachings provided herein may be implemented in a number of different manners.

Embodiments which use patient images for prediction of treatment outcome using a treatment outcome prediction system will now be described. The treatment outcome prediction system may use volumetric patient imaging to provide a platform for a clinician to plan interventional treatments for pulmonary disease and to receive predicted outcomes for the planned interventional treatment from the system. One example of the steps of a treatment planning and outcome prediction procedure which may be performed by the treatment planning and outcome prediction system is shown in the flowchart depicted in FIG. 3. However, it should be understood that the steps described herein need not necessarily all be performed or need not necessarily be performed in the order presented and various alternatives also exist.

The treatment planning and outcome prediction procedure begins at the starting step 30 at which a clinician interacts with the system to direct it to begin a new treatment outcome prediction procedure, which may be a part of a treatment planning procedure. The clinician may select the volumetric patient volumetric images or imaging data to be used for the treatment planning procedure and the system may receive the volumetric images or imaging data in step 32 as well as other patient data. The volumetric patient images may be patient images or imaging data produced by CT scans, MM scans, and/or PET scans, for example, from which a series of two-dimensional planar images (referred to herein as two-dimensional volumetric images or two-dimensional images) can be produced in multiple planes, for example. Other patient data which may be received by the system and which may be useful in the treatment planning process includes the patient's emphysema score, lung function test results such as FEV1, and collateral ventilation measurements. For example, the amount of collateral ventilation may have been determined by direct measurement using a bronchoscopic system such as the CHARTIS System. Alternatively, measurements like collateral ventilation may be predicted at a later step using predictors as described herein.

Next in step 34 the system analyzes the patient data. For example, the system may analyze the volumetric images to segment and identify the airways, the lobes, the sublobes, the fissures, and/or other features of the lungs. Software for analyzing volumetric images of the lungs includes 3D imaging software such as the Apollo quantitative pulmonary imaging software. Methods of identifying and characterizing sublobes are described in U.S. Pat. Pub. No. 2012-0249546, entitled Method and System for Visualization and Analysis of Sublobar Regions of the Lung, which is hereby incorporated by reference. Methods of identifying and characterizing the pulmonary fissures are described in U.S. patent application Ser. No. 13/804,542, entitled Visualization and Characterization of Pulmonary Fissures, which is also hereby incorporated by reference. The methods used by the 3D pulmonary imaging software and the U.S. patent applications listed above may be likewise used to analyze the volumetric images for treatment planning as described herein. Step 34 may include analyzing the patient data for generating 3D images. However, the same analysis may also be performed to detect and/or quantify predictors, whether or not a 3D image is actually generated.

Figure 3:
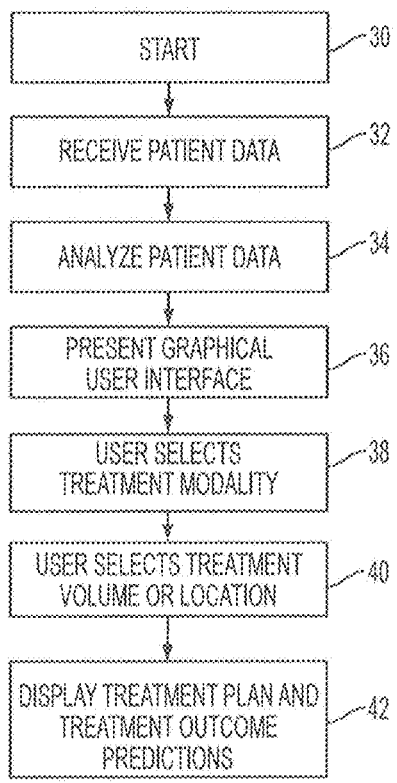
FIG. 3 is an example of a method of treatment planning and outcome prediction.

After the system has analyzed the patient data, the system may create a graphical user interface in which a 3-dimensional model of the airways is presented along with other elements that may be used by the clinician during treatment planning in step 36 of FIG. 3. The graphical user interface may include display predictions about the patient's disease form, lung characteristic (such as the presence of collateral ventilation, fissure integrity, etc.), outcome predictions, and/or probability of adverse events as determined by quantitative CT analysis. An example of a graphical user interface is shown in the screenshot depicted in FIG. 4. The screenshot 100 includes a 3-dimensional model of the patient's lungs 102 constructed by the system from the volumetric imaging data. In this example, the upper lobes are displayed in a different color (represented by light gray) and demonstrate how the different lobes can be visualized. Alternatively, the sublobes may be displayed in different colors, for example. There is also a device selection window 104 and may also include a device diagram window (not shown). Once a device has been selected by the clinician, it may be identified in the device selection window 104 and shown in the device diagram window.

Figure 4:
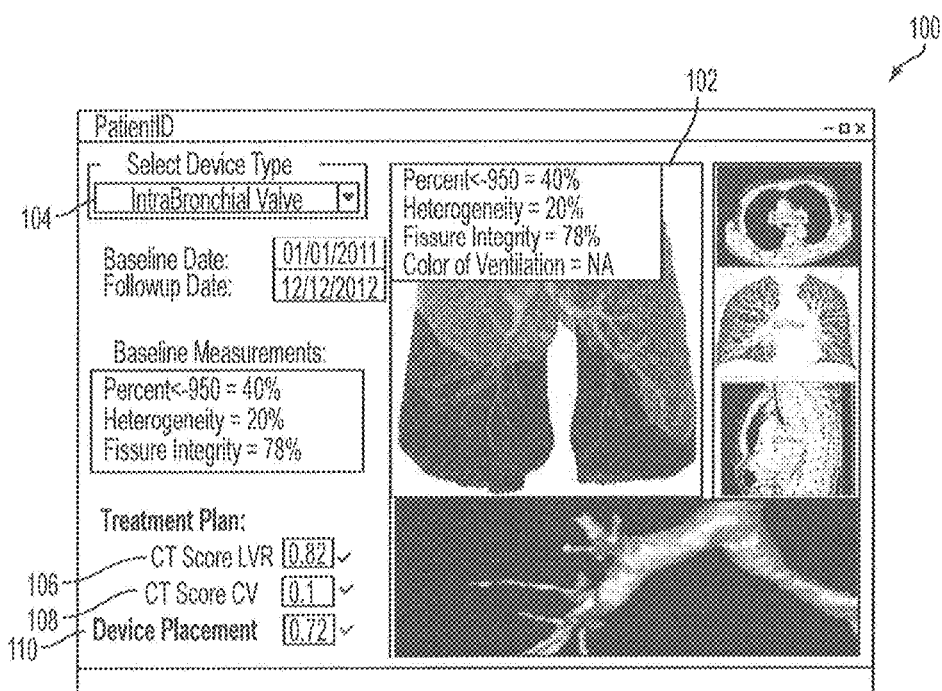
FIG. 4 is an example of a user interface for treatment planning and outcome prediction.

The user interface may also include predictions based upon analysis of the patient images using a prediction model as described here. In FIG. 4, the user interface includes a prediction of the likelihood of a successful lung volume reduction 106, a prediction of collateral ventilation 108, and a prediction of proper valve placement 110. The values presented may be indicative of the percent likelihood and may be shown as a percent or a decimal fraction of one or less, or as any other value representing likelihood. Alternatively, the values may be shown as present/not present (absent). In another alternative, the values may be presented as numerical scores indicating predicted amounts. For example, in the values shown in FIG. 4, the "CT score CV" of 0.1 represents a 10% likelihood of collateral ventilation. Alternatively or additionally, any other types of prediction or scores could be shown, and alternative nomenclature or abbreviations may be used. For example, the display may include predictions of the likelihood of success and/or of adverse events for various treatment modalities, and or may display a preferred treatment modality, based upon these or other predictions. The predictions provided by the system may be determined and displayed by the system before a particular treatment and/or treatment location is selected by a clinician, such as to give a general indication of the likelihood of success, for example. In some embodiments, the predicted features determined in this step may be used to triage patients into those who are eligible for particular procedures including endoscopic lung volume reduction procedures such as valve placement, coil placement, energy delivery, or biosealant delivery, and those who are not eligible. The results of this triage may be provided to the clinician on the display.

Next, the clinician may select a particular treatment modality in step 38 and treatment location or treatment volume in step 40 of FIG. 2. Alternatively, the clinician may select a treatment modality earlier, such as between steps 32 and 34. One or more of the treatment predictions may vary depending upon the treatment modality, location, or volume, such as the likelihood of lung volume reduction or likelihood of a positive result. Therefore, after these selections are made, the predicted features and outcomes may be determined for the first time, or may be determined again now more specifically by taking into account these selections, and may be displayed for the clinician. That is, one or more predictions may be calculated and displayed earlier, such as immediately after analysis of the patient data in step 34. One or more of these predictions may then be optimized and displayed again, and/or one or more other predictions may be displayed, after the user selects the treatment modality in step 38 and the treatment volume in step 40.

In step 42, the system may display the treatment plan which may include the selected treatment modality, treatment volume, treatment location, and/or treatment pathway on the 3-dimensional airway model. The display may further include a display of predictions calculated by the system using predictors including predicted likelihood of successful outcome and/or risk of adverse events (such valve placement errors, pneumothorax, and/or death) and the patient's volumetric images and in some cases the selected treatment plan. For example, the display may include predicted features such as collateral ventilation and/or predicted outcome such as likelihood of success and likelihood of an adverse event such as pneumothorax. The predictions provided in this step may be refined based on the treatment plan as compared to predictions that may have been provided in step 36. The planned treatment as displayed may be performed on the patient in accordance with the plan.

Figure 5:
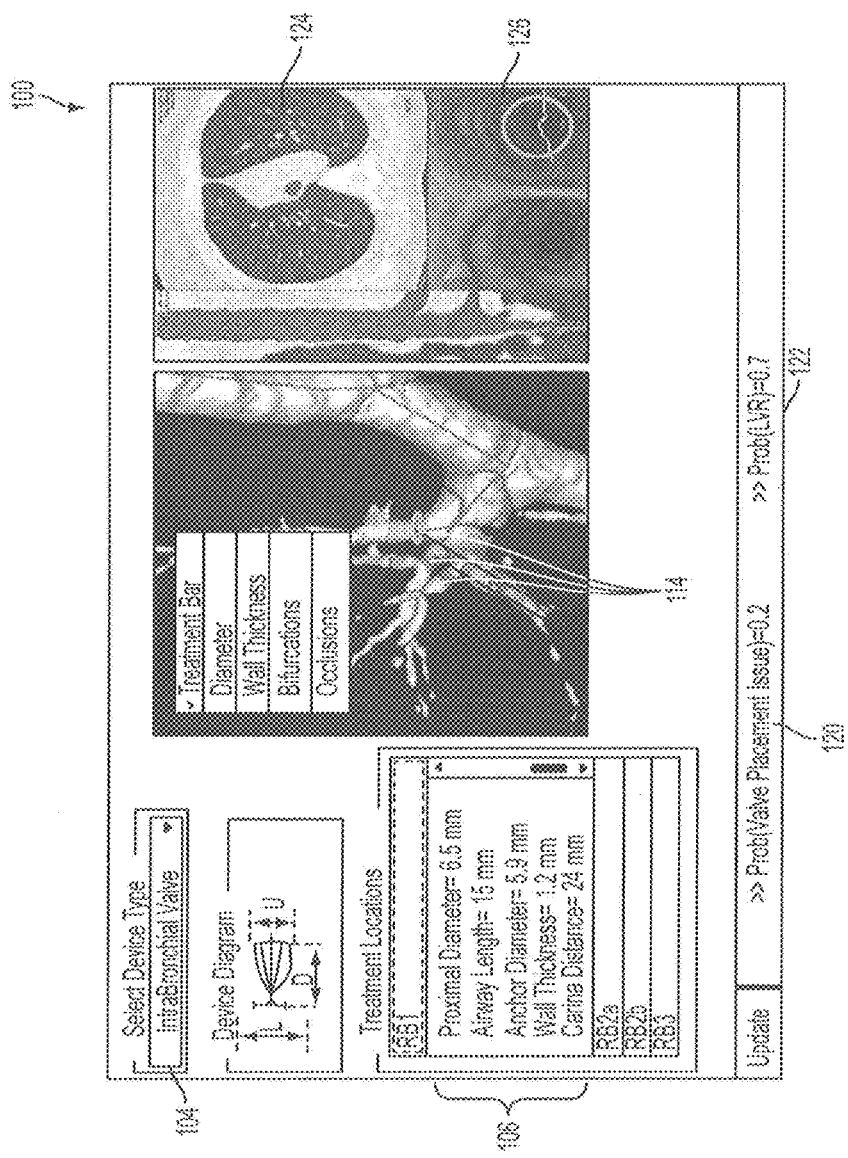
FIG. 5 is an example of a user interface for displaying a treatment plan including outcome prediction.

An example of a display of a treatment plan is shown in FIG. 5, which includes a screenshot 100 with a 3-dimensional model of the patient's airway to be treated 112 with an indication of the treatment locations 114 and a display of the physical characteristics of the airways to be treated 116. The display further includes a device selection window 104 in which an intrabronchial valve has been selected, and a display of the probability of a valve placement error 120 and the probability of a successful lung volume reduction 122. This example further includes other elements which may be useful, including a 2 dimensional CT image of the lungs and a virtual bronchoscopy image 126.

In addition to predicting treatment outcome, various embodiments may be used to predict features of the patient's lungs. With regard to the prediction of collateral ventilation, it is noted that such a prediction may be considered as intra-lobar or inter-lobar collateral ventilation. Intra-lobar collateral ventilation may occur through the accessory pathways of the lungs including the intra-alveolar pores of Kohn, the bronchioalveolar communications of Lambert and the intrabronchiolar pathways of Martin. In certain conditions, such as emphysema, these accessory pathways can become enlarged and airway obstruction can increase expiratory resistance, leading to the passage of air as intra-lobar collateral ventilation from one lobule to another. Interlobar collateral ventilation may occur when portions of the interlobar fissures are absent or when the adjacent lobes become fused to each other, resulting in an incomplete fissure and allowing air communication between the lobes at those locations.

Predictors of collateral ventilation may include the following: contralateral lung lower lobe tissue to air ratio, which is the tissue to air volume ratio in the lower lobe of the contralateral lung and may be abbreviated CL_LL_TAR; fissure integrity for the fissure touching the targeted lobe which may be abbreviated FI; contralateral lung lower lobe emphysema percent which may be abbreviated CL_L-L_Emph and which may be measured as the percentage of emphysema below a threshold value, such as below −950 HU, −920 HU, −910 HU, or −856 HU, for example; airway minimum inner diameter among the treated airways which may be abbreviated MinInnerDiam and which is the smallest inner diameter of the planned treated airways; maximum tapering along the planned treated airways which may be abbreviated MaxTapering; and minimum wall area percentage among the treated airways (MinWAF), which is the area fraction that the airway wall occupies relative to the area described by the outer wall and may be abbreviated MinWAF. Other predictors could also be identified by evaluation of the volumetric images in the training database. MinWAF is a unit-less value that lies in the range of 0 to 1. MaxTapering is the maximum airway tapering among the treated airways in the targeted lobe and may be calculated as described further below. The fissure integrity score can be computed as the percentage of completeness of the fissure.

It provides a global quantitative assessment of possible collateral ventilation. With a fissure completeness of 100%, the fissure is intact and collateral ventilation between adjacent lobes is unlikely. In contrast, with a fissure completeness score of 0%, there is a possibility of collateral ventilation since no fissure serves as a seal between abutting lobes of the lung. The fissure integrity may be evaluated and scored as described in U.S. patent application Ser. No. 13/804,542, the disclosure of which is hereby incorporated by reference.

Figure 6:
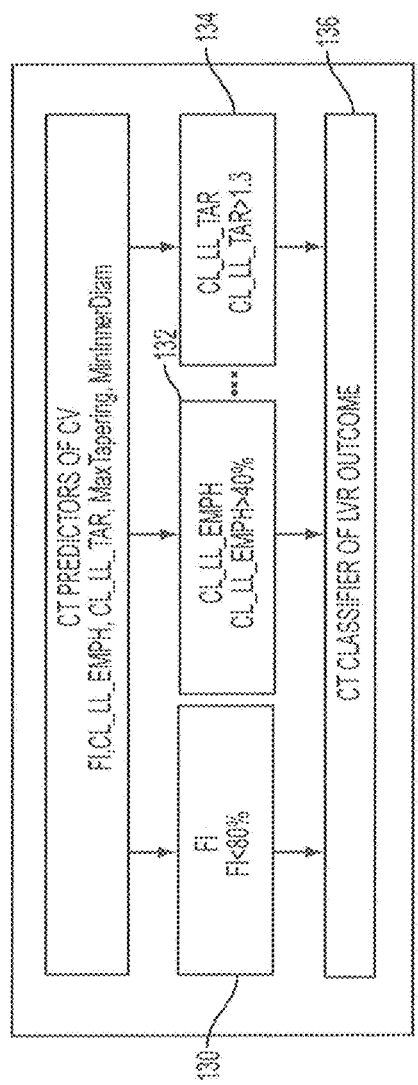
FIG. 6 is another example of a schema for prediction of an outcome of a lung volume reduction procedure.

Airway taper is an indication of whether an airway is getting larger or smaller as the airway extends distally, with a normal airway ideally growing narrower as it proceeds distally. It may be calculated as:

$$\frac{\text{Inner Lumen Area (40}^{th}\text{ percentile)} - \text{Inner Lumen Area (70}^{th}\text{ percentile)}}{\text{Inner Lumen Area (40}^{th}\text{ percentile)}}$$

in which the percentile refers to the percentage of the centerline length, from the parent to the bifurcation to the next bifurcation, of the location at which the measurement is taken. Other methods of calculating airway taper are also possible and may alternatively be used. These predictors may be used alone or in combination to predict the likelihood of collateral ventilation, and this may further be used to determine whether a patient may be eligible for lung volume reduction treatment. For example, in the basic schema shown in FIG. 6, the fissure integrity score 130, the contralateral lower lobe emphysema score 132, and the collateral lower lobe tissue to air ratio 134 may be used as predictors of lung volume reduction outcome 136 in a simple rule-based classifier to exclude candidates for lung volume reduction who are likely to have collateral ventilation. Cut-off values may be selected for each of the parameters, such as those shown in FIG. 6. For example, in this classification system, if the fissure integrity score is greater than 80%, the contralateral lower lobe emphysema score is less than 40%, and the collateral lower lobe tissue to air ratio is less than 1.3, the patient may be classified as not having collateral ventilation. In such a case, lung volume reduction may be recommended. However, if the patient fails to meet one of these thresholds, the patient may be classified as having collateral ventilation and lung volume reduction using valves may not be recommended. This model demonstrates how the predictors may be used, but more sophisticated models may also be used, such as classification models in which the values of the predictors themselves (rather than the presence or absence of meeting a threshold) may be used in combination to classify a patient.

Another feature that may be predicted using predictors in a volumetric image is the likelihood of problems with valve placement. Difficulties with valve placement can have a significant impact on the outcome of endobronchial lung volume reduction procedures. In some cases, the problems could relate to procedural errors during valve placement. In other cases the problems may be due to patient anatomy and/or device fit, such as placement of a valve in an unintended location, such as in a branch distal to the intended location or in a bifurcation of an intended airway, or air leak may occur around a valve that allows the distal airways to remain open. Predictors may be used to evaluate the risk of these types of valve placement problems. Examples of predictors of valve placement problems include: centerline length, which is the centerline length of airway branches in which the valve is to be placed; aspect ratio, which is the ratio of the centerline length to the average inner airway area in the airway branch, and which gives insight into the shape of an airway; tapering, as described above; diameter of the target location; and wall area fraction, which is the cross-sectional area of the airway wall relative to the total cross-sectional area of the airway including the wall and the lumen. These predictors may be determined by extraction from the airway segmentation, for example. Other predictors could also be identified by evaluation of the volumetric images in the training database. A schema to predict problems with lung valve placement may be based on these parameters. The schema may be derived according to the type of lung valve selected (such as endobronchial or intrabronchial). Several types of classifiers can be deployed using the predictors, including rule based classifiers, tree-based classifiers, Naïve Bayes classifier, and more sophisticated classifiers.

In addition a likelihood of a valve placement with no misplacement, which may be abbreviated or indicated by the words Device Placement, can be computed after an initial path of a treatment plan is determined. It can be re-computed after adjustment of the targeted airway location until it is optimized.

Other features that may be predicted using predictors in the volumetric images include the likelihood of adverse events and calculated lung compliance. For example, lung compliance may be predicted using degree of emphysema, air trapping and ventilation distribution derived from registering the inspiratory and expiratory scans of a given subject. Additional predictors may also be used. Alternatively, lung compliance can be measured using a lung function study to determine residual volume.

Figure 7:
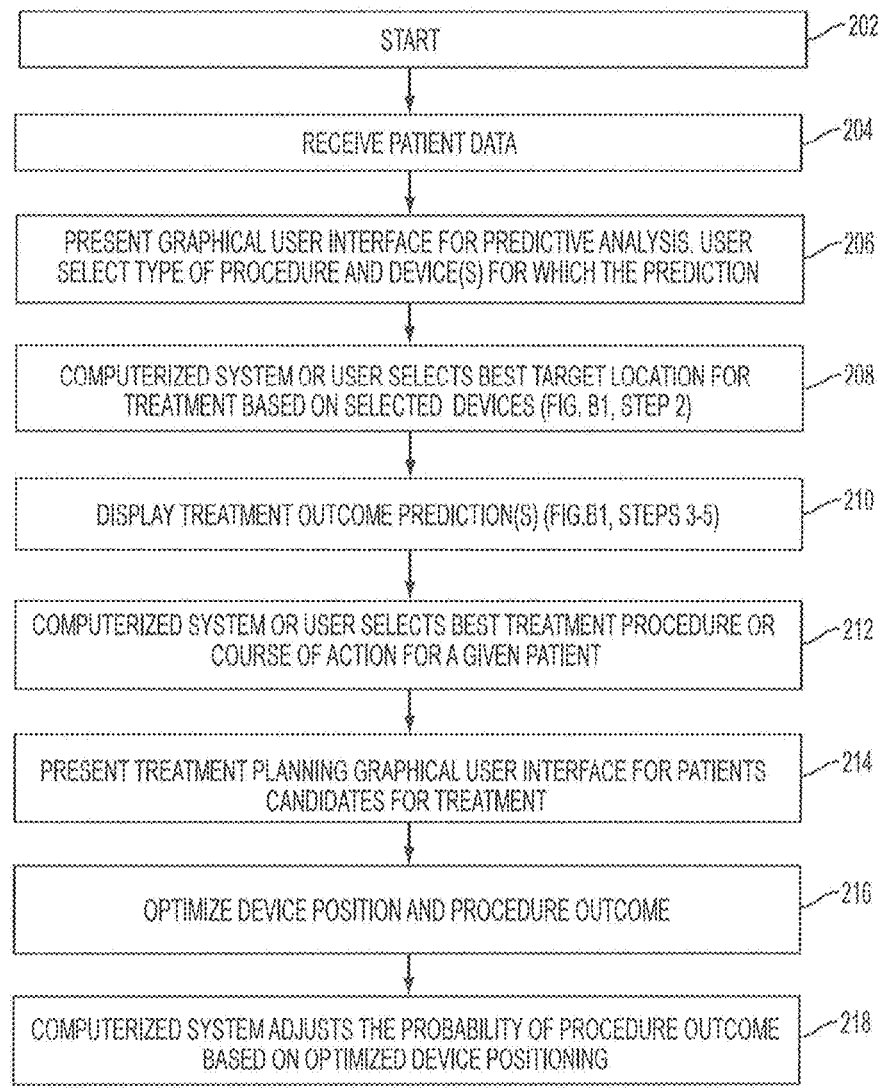
FIG. 7 is another example of a method of treatment planning and outcome prediction.
Figure 8:
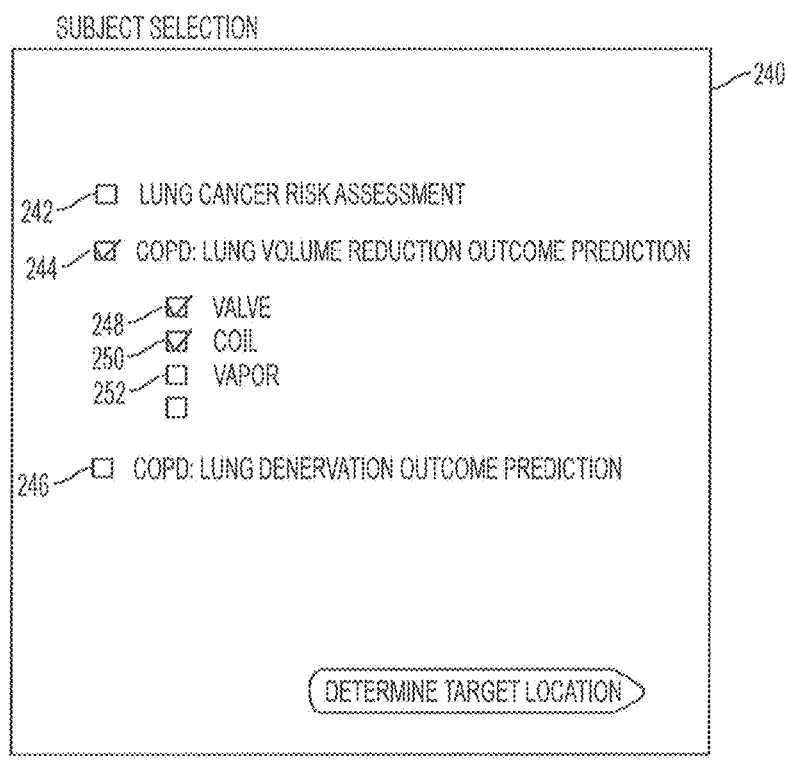
FIG. 8 is an example of a user interface for selecting lung cancer risk assessment and treatment outcome prediction.

An alternative method of treatment outcome prediction and treatment planning is shown in the flow chart in FIG. 7. The method starts at step 202, and then the system receives patient data at step 204, which may be any of the patient data as described previously and may include patient images. In step 206 the system presents a graphical user interface to the user, which may include options for types of procedure and types of devices for which prediction analysis will be conducted. An example of such a graphical user interface is shown in FIG. 8. In this example, the user may select between various options on the user interface 240 including a lung cancer risk assessment box 242, a lung volume reduction outcome prediction box 244 and a lung denervation outcome prediction box 246. Other options for prediction may also be included, and further sub options may be provided for selection by the user within each option. For example, within the option of lung volume reduction procedure, the user may select one or more specific modalities. In the example shown in FIG. 8, these modalities for selection include a valve box 248, a vapor box 250, and a coil box 252, though additional and/or alternative options may also be provided. The user may select one or more desired options for prediction by clicking the box on the graphical user interface, after which the selected option or options are shown as checked or otherwise indicated.

Figure 9:
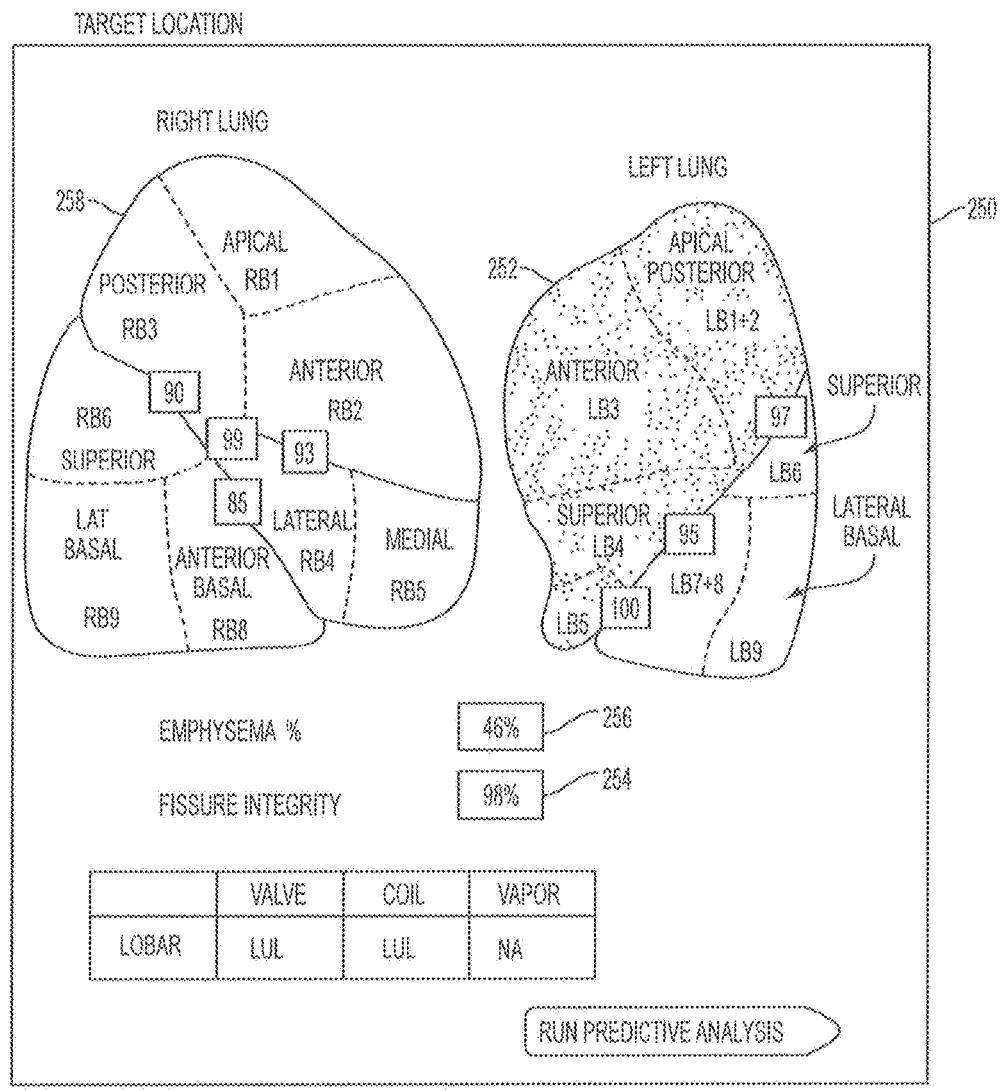
FIG. 9 is an example of a user interface for treatment planning and outcome prediction.

After a treatment modality and/or device are selected, the user or the system may then select a treatment location in step 208. For example, the user may select the treatment location by selecting a location on a graphical user interface including a 3-dimensional display of the patient's lungs. Alternatively, the system may determine a best target location for treatment using the patient data, and the selected location may be displayed for the user on a 3-dimensional display of the patient's lungs. For example, the system may determine the best treatment location based upon analysis of the patient's images, such as the best location as determined based upon key measurements and predictors such as percent emphysema, fissure integrity, and vessel measurements such as at various locations, such as in each lobe or sublobe, and/or across the lungs. In some embodiments, the system may select a treatment location which may be displayed on the user interface, and the user may either accept the treatment location or override the selection and select a new treatment location using the user interface. Once a treatment location is selected either by the user or by the system, the lobes selected for treatment may be highlighted, colored, or otherwise displayed in a manner to distinguish them from the untreated lobes. An example of such a display is shown in FIG. 9, which depicts a graphical user interface 250 after a treatment location has been selected. In this example, the lobe selected for treatment 252 is the left upper lobe, which is displayed in a different color than the remainder of the lung. The graphical user interface further includes identification of each lobe, a fissure integrity score 254 for fissure portions between pulmonary segments, the percentage of emphysema 256 in the lobe to be treated, and the fissure integrity of the entire fissure of the lobe to be treated. Each of these may be automatically calculated by the system and provided on the graphical user interface 250 along with the images of the lung 258.

Once a treatment location is selected, the system may calculate and display outcome predictions in step 210. These predictions may vary depending upon the type of treatment modality or device. The predictions may be provided separately for each possible treatment modality or device selected by the user at step 206, for example, either on the same display or on separate displays. Examples of displays of outcome prediction are shown in FIGS. 10-12.

Figure 10:
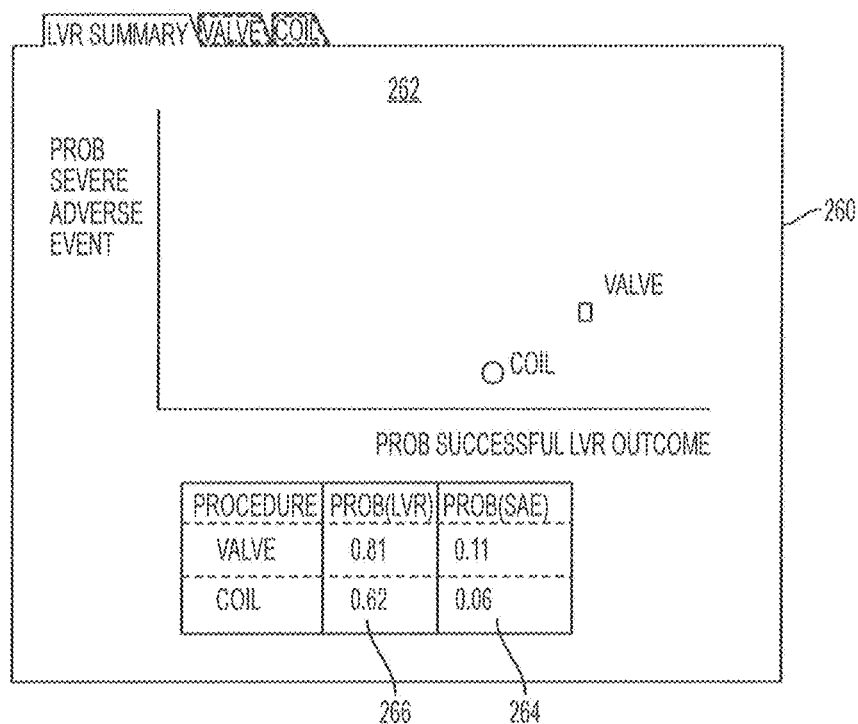
FIG. 10 is an example of a user interface for treatment planning and outcome prediction.

In FIG. 10, the display 260 includes a visual representation 262 of the probability of a severe adverse event and the probability of a successful LVR outcome are shown on opposing x and y axis in the manner of a graph. The display 260 shown is a summary, identified as an LVR Summary, and both selected treatment modality options, which in this example are valve and coil, are shown. The numerical values for the probability of a severe adverse event 264 and of a successful LVR outcome 266 are also shown for each selected treatment modality in this example. The user may select displays which show additional data for each treatment modality separately, such as by clicking on the icons, which may be tabs as shown in this example.

Figure 11:
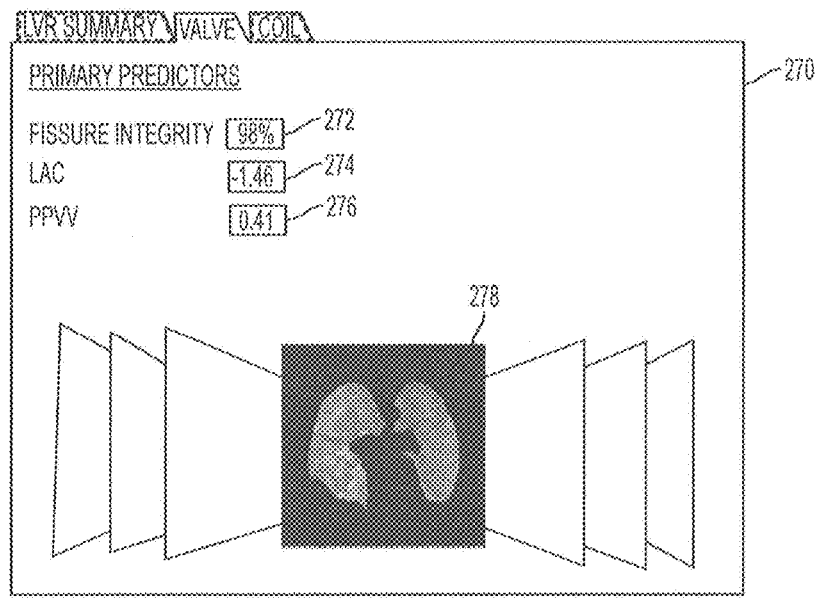
FIG. 11 is an example of a user interface for treatment planning and outcome prediction for valve placement.
Figure 12:
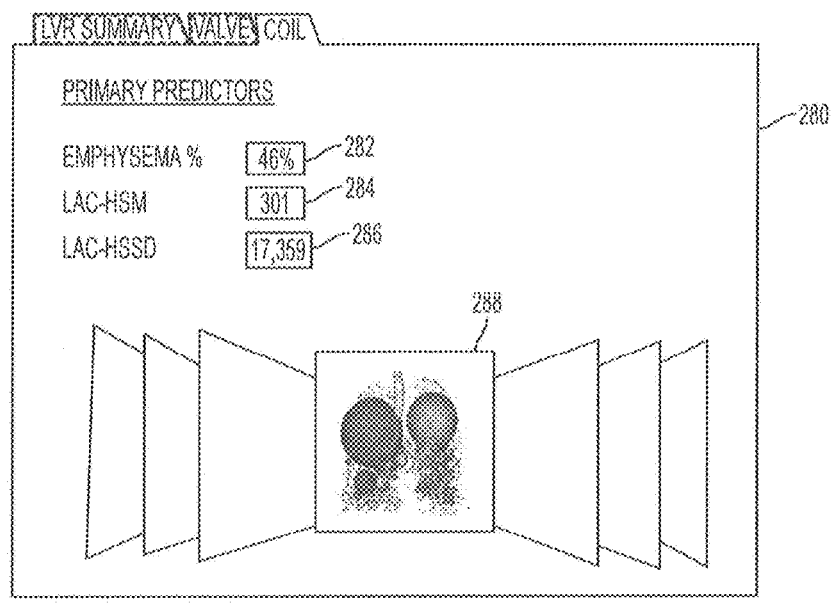
FIG. 12 is an example of a user interface for treatment planning and outcome prediction for coil placement.

FIGS. 11 and 12 present the visual displays of prediction for valve placement and coil placement, respectively, at the selected location. The display includes a list of predictors as well as the results as determined by the system. In this example shown in FIG. 11, the visual display 270 includes the predictors fissure integrity 272, LAC 274 (low attenuation cluster slope which is the slope α of the log-log plot of number of emphysematous holes versus hole size), and PPVV 276 (percentage of peripheral vessel volume, which is the volume of the most distal vessels relative to the overall volume of all vessels) for valve placement at the selected location. The main predictors were: fissure integrity; percentage of peripheral vessel volume, which is the volume of the most distal vessels relative to the overall volume of all vessels, and is abbreviated PPVV in table 1; low attenuation cluster slope which is the slope α of the log-log plot of number of (emphysematous) holes versus hole size and is abbreviated LAC in Table 1

In FIG. 12, the visual display 280 includes the predictors of percent emphysema 282, LAC-HSM 284, and LAC-HSSD 286, in which LAC-HSM is the mean hole size of emphysema bullae and LAC-HSSD is the standard deviation (and therefore an indication of the variability) of emphysema hole sizes. The displays may also include an image or representation of the lungs or part of the lungs. In FIG. 11, the visual display 270 includes an image of the lung fissures 278, with the fissure shown in two contrasting colors showing fissure that is present distinct from fissure that is absent. In FIG. 12, the display 280 includes a visual representation of the lungs 288 showing a representative depiction of emphysema in different portions of the lungs. The emphysema depictions are each provided in a different color in different lobes, and the amount of emphysema at a location is represented by the size of the spheres, with larger spheres representing a greater amount of emphysema. The images of pages to the sides of the lung figures may be selected by the user to display other pertinent visual representations illustrating the distribution of the main predictors that may be provided for review and browsing.

These predictions shown in FIGS. 10-12, for example, may be useful for a user for selecting which treatment modality to employ in a patient. In a next step 212 of FIG. 7 the treatment modality or device is selected, either by the system or by the user. The user may select the treatment modality or device by inputting the selection using a graphical user interface and the system may receive the user's selection. Alternatively, the system may select the best treatment modality based upon the outcome predictions determined for the treatment location. The user may have the option to override the selection made by the system and select a different treatment modality or device and enter that selection into the system using the user interface.

Once the treatment modality or device has been selected in step 212, the system and user may proceed with treatment planning. The system may present a treatment planning graphical user interface in step 214 and the user may interact with the system to plan the treatment for the patient as described previously above. The user may optimize device position or adjust the treatment location to improve the procedure outcome in step 216 and the system may update the outcome probability predictions based upon the optimized device positioning in step 218. For example, the user may optimize the device position or treatment location adjusting the treatment location, such as moving the device proximally or distally in the same branch, or to a next proximal or distal branch, or to a new location, from that initially selected by the user or system. These updated outcome predictions may be used by the user in selecting the optimized treatment location and may be displayed for the user on a graphical user interface as part of a final treatment plan. This optimized treatment plan may then be performed on the patient.

Figure 13:
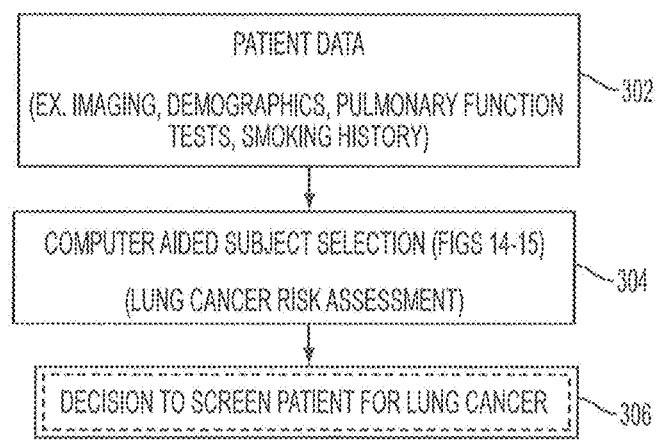
FIG. 13 is an example of a method of lung cancer risk assessment.
Figure 14:
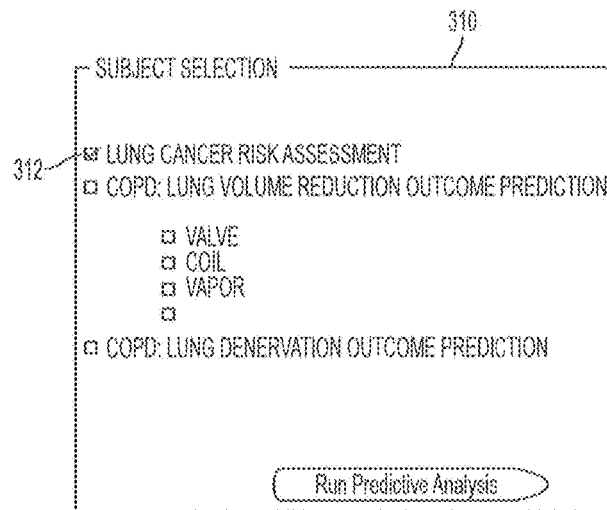
FIG. 14 is an example of a user interface for selecting lung cancer risk assessment and treatment outcome prediction.
Figure 15:
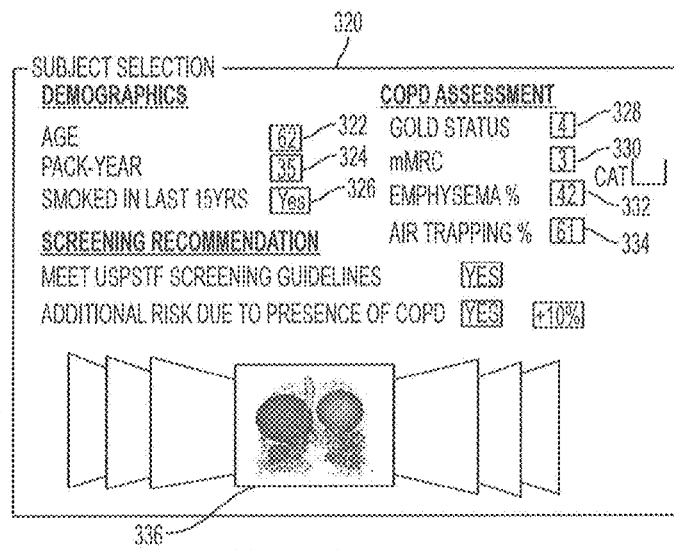
FIG. 15 is an example of a user interface for lung cancer risk assessment.

Another embodiment is shown in the flow chart displayed in FIG. 13. In this embodiment, the system may be used for predicting the risk of lung cancer and recommending lung cancer screening. In step 302, patient data as described previously may be entered into the system which may include data relevant to lung cancer risk, such as patient images, demographics such as age and gender, pulmonary function test results, and smoking history such as amount and duration of smoking (number of pack years). In step 304, the user may select, using a graphical user interface, the assessment to be performed by the system, which in this example is lung cancer risk assessment. An example of a user interface which may be used for this selection is the interface 310 shown in FIG. 14, in which the user has selected lung cancer risk assessment box 312 to direct the system to perform lung cancer risk assessment. The system may then analyze the patient data to determine lung cancer risk, including analysis of the images using lung cancer predictors, and the results of the analysis may be displayed for the user on a new graphical user interface, along with lung cancer screening recommendations in step 306. An example of such a graphical user interface is shown in FIG. 15, which is a visual display 320 in which the patient demographics are shown, including age 322, number of pack-years the patient has smoked 324, and whether or not the patient has smoked in the last 15 years 326. Other demographics may be included additionally or alternatively. The graphical user interface also displays various COPD assessments which have been determined by the system or input into the system, as patient data, including Gold Status 328, mMRC 330, which stands for modified Medical Research Council Dyspnea scale, percent emphysema 332, and percent air trapping 334. The graphical user interface in this example further includes an image 336 which is a representation of the amount of emphysema in the lungs as described previously. Finally, the system displays whether lung cancer screening is recommended. In this example, the recommendation is a yes or no indication 338 based upon meeting the USPSTF screening guidelines, but other guidelines may be used. Alternatively, lung cancer predictors may be used which were developed using the databases as described herein. For example, the risk of lung cancer may be determined using demographic data and smoking history as well as the presence of COPD and lung health evaluation based upon analysis of the patient images and lung cancer risk models. In this example, the display further includes a yes or no indication 340 of whether or not COPD is present, and provides a numerical value of the amount of additional risk 342 due to the present of COPD, which in this example is 10%. The presence or absence of COPD may be determined, wholly or in part, using predictors as determined using the databases as previously described. In some embodiments, the display 320 may include specific lung cancer screening recommendations, such as type of screening and frequency of screening recommended. Screening may then be performed on the patient in accordance with the recommendation presented on the display.

EXAMPLE 1

Valve misplacements due to complex anatomy have been previously reported but little was known about anatomical factors linked to these procedural issues. In this example, the anatomical properties leading to optimal delivery of a valve to a targeted airway were investigated.

The CT scans of 184 subjects were retrospectively analyzed. The subjects had severe emphysema and had undergone an LVR procedure following a unilateral complete occlusion protocol. The CT images included baseline images (obtained prior to the procedure) and images obtained at 3-months follow-up. The follow-up scans were used to assess the presence or absence of valve placement problems. When valve placement problems were identified, they were classified as Type I or Type II. Procedural errors due to valves not being located in the targeted branch, i.e., being located partially or entirely in a sub-segmental branch, were identified as Type I error. Lack of airway collapse distal to valve placement, either due to air leak around the valve or collateral ventilation, was identified as a Type II error.

Quantitative CT measurements of the treated airway segment were extracted at 547 valve placement locations in baseline scans of the subjects to provide insight into the shape and morphology of treated airway branches. The measurements were: centerline length; average lumen diameter; circularity, wall thickness (WT), wall area fraction (WAF) measured as the fraction that the area of the airway wall adjacent to the valve relative to the area of the entire airway branch in which the valve was placed; tapering, measured as the ratio of inner airway area of the distal end relative to the proximal end of the airway branch; and the aspect ratio, measured as the ratio of centerline length to the average inner airway area. All quantitative CT measurements were automatically computed using Apollo software (VIDA Diagnostics).

The seven airway measurements as well as data including the valve type (endobronchial or intrabronchial), the treated lobe, and the presence or absence of valve placement errors were used to feed a logistic regression analysis to determine quantitative CT predictors of valve placement errors. A generalized estimating equations (GEE) method accounted for correlation between measurements. Type I errors were present in 19.6% (107/547), Type II errors were present in 38.2% (209/547), and in 42.2% (231/547) there were no valve placement errors. Valve type and lobe did not have an effect on the occurrence of valve placement errors. However, three predictors were identified as significant by regression analysis: wall thickness ($p=0.0097$); wall area fraction ($p=0.01$ when $0.62<WAF\leq0.65$ vs. $WAF>0.65$; $p<0.001$ when $WAF<=0.62$ vs. $WAF>0.65$); and tapering ($p<0.001$ when tapering$\leq0.13$ vs. tapering$>0.13$). Smaller wall thicknesses and greater wall area fraction and tapering are associated with lower probability of valve problems, which is typical of smaller airways.

Figure 16:
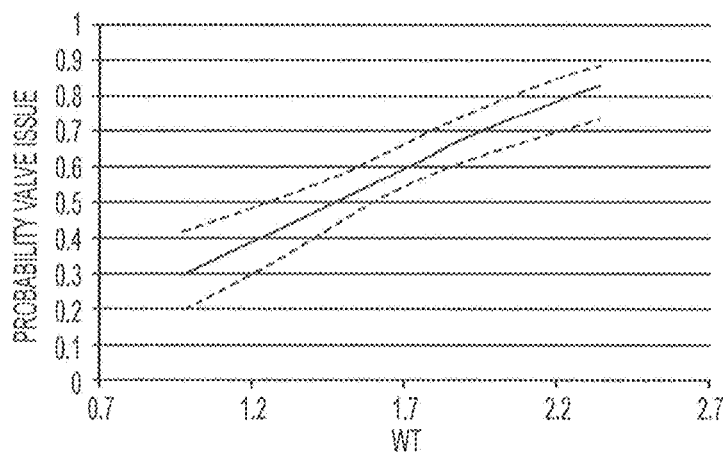
FIG. 16 is a graph of wall thickness verses the probability of valve placement errors.
Figure 17:
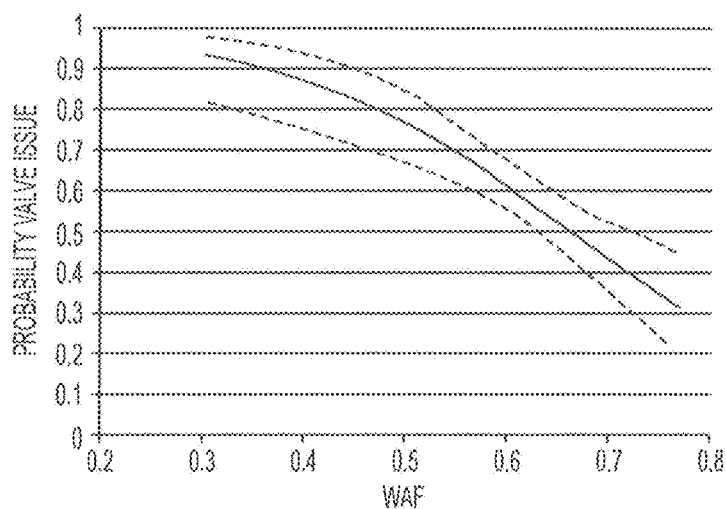
FIG. 17 is a graph of wall area fraction versus the probability of valve placement error.
Figure 18:
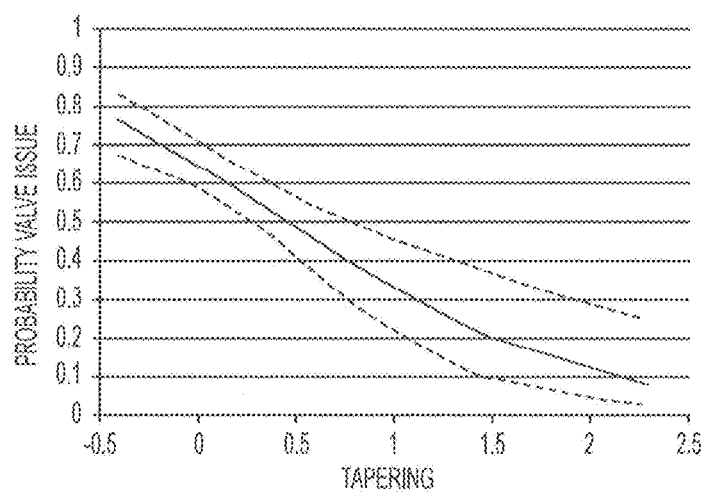
FIG. 18 is a graph of tapering versus the probability of valve placement error.

The results of this example are shown graphically in FIGS. 16-18. FIG. 16 is a graph of wall thickness verses the probability of a Type I or Type II valve errors. Likewise the probability wall area fraction and tapering and valve errors are shown versus in FIGS. 17 and 18, respectively. In each case, the solid line represents the calculated probability and the dashed lines represent the confidence interval.

This example shows that quantitative CT analysis can help identify airways for optimal anatomic fit for valves, thereby reducing the probability of procedural issues and providing an objective and more efficient approach to treatment planning.

EXAMPLE 2

In this example, the relationship between lung volume reduction and the occurrence of pneumothorax was retrospectively analyzed using CT images. CT scans of 183 subjects with severe emphysema were analyzed. The subjects had all undergone lung volume reduction with valves were following a unilateral complete occlusion protocol. The CT scans were acquired at Total Lung Capacity (TLC) and included a baseline scan and a follow up scan at 3 months after the procedure. The volumes of treated lobes were measured on the baseline and 3-month follow-up CT scans. Post-procedural pneumothorax events were identified and valve placement errors were studied retrospectively by analyzing follow-up CT images. Thirty-five baseline variables including confounding variables (personal characteristics as described above), CT quantitative measurement of fissure integrity (FI), density, and vessel measurements were used to feed a logistic regression analysis in order to find significant predictors of lung volume reduction outcome.

Quantitative CT measurements were extracted from the baseline CT scans and computed using dedicated lung Quantitative Imaging software (Apollo®, VIDA Diagnostics, Coralville, Iowa). Lobar volumes were also measured on both baseline and follow-up scans. A lobar volume reduction greater than 350 cc was used to identify a positive response to the lung volume reduction procedure.

Of the total group, 12% (22/183) experienced one pneumothorax event, with the following lobar distribution: left lower lobe (n=12), left upper lobe (n=6), right lower lobe (n=3), and right upper lobe (n=1). A predominance of pneumothorax events occurred in the left lung and in the lower lobes, in particular the left lower lobe ($p=0.02$).

Figure 19:
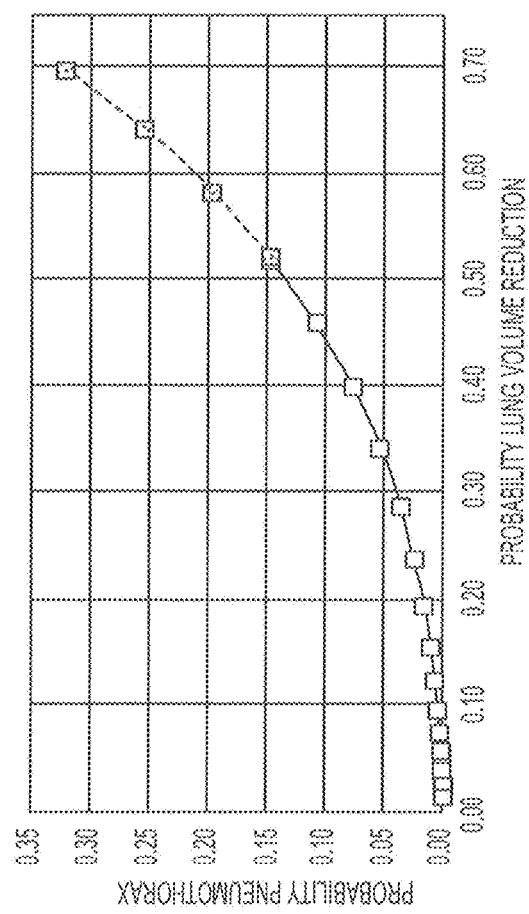
FIG. 19 is a graph of the probability of pneumothorax versus the probability of successful lung volume reduction.

A regression analysis was performed on the data to identify the main quantitative CT predictors of pneumothorax following lung volume reduction procedures. The identified predictors were the fissure integrity of the treated lobe ($p=0.01$) and the volume of the treated lobe ($p=0.01$). Hyper-inflated lobes and complete fissures commonly associated with successful lung volume reduction procedures were thus associated with a higher probability of pneumothorax. A graph showing the trade-off between successful lung volume reduction and the occurrence of pneumothorax is shown in FIG. 19. The modeling of the lung volume reduction/pneumothorax trade-off in FIG. 19 shows a steady increase of pneumothorax events when the probability of a successful lung volume reduction procedure exceeds 50%. When there were no valve placement errors, the probability of a pneumothorax event was significantly higher (probability of 16%) than when one or few valve placement errors occurred (probability of 6%) impairing the lung volume reduction procedure results.

The probability of a pneumothorax event in an endobronchial valve lung volume reduction procedure following a unilateral partial occlusion protocol was found to be inversely related to a successful lung volume reduction (with a lung volume reduction greater than 350 cc). Quantitative CT can be used to measure predictors of pneumothorax and successful lung volume reduction to determine the risk of pneumothorax and whether a lung volume reduction procedure is likely to be effective for a patient in clinical practice, as well as to evaluate the tradeoff between the risks and benefit of the procedure.

EXAMPLE 3

This example was performed to evaluate the relationship between fissure integrity and lung volume reduction procedure outcome. CT scans of 183 subjects with severe emphysema were analyzed as in Example 2. The subjects had all undergone lung volume reduction with valve placement following a unilateral complete occlusion protocol using either endobronchial valves (Zephyr™ valves from Pulmonx Inc.; n=37) or intrabronchial valves (IBV® valves from Olympus Medical Co.; n=146). The CT scans were acquired at full inspiration and included a baseline scan prior to the procedure and a follow up scan at 3 months after the procedure. Volumes of treated lobes were measured on baseline and 3-month follow-up CT scans, and a lobar volume reduction greater than 350 cc was considered to be indicative of positive response to treatment. Thirty-five baseline variables including confounding variables (personal characteristics as described above), CT quantitative measurement of fissure integrity (FI), density, and vessel measurements were used to feed a logistic regression analysis in order to find significant predictors of lung volume reduction outcome, as in Example 2. All the quantitative CT measurements were automatically computed from the CT scans using dedicated lung Quantitative Imaging software (Apollo, VIDA Diagnostics), with access to lobe editing for precise density, vessel and fissure integrity measurements.

After elimination of highly correlated variables and stepwise regression analysis, the main quantitative CT predictors which were correlated to successful lung volume reduction are shown in Table 1 below. The main predictors were: fissure integrity; percentage of peripheral vessel volume, which is the volume of the most distal (segmented) vessels relative to the overall volume of all (segmented) vessels and is abbreviated PPVV in Table 1; low attenuation cluster slope which is the slope α of the log-log plot of number of (emphysematous) holes versus hole size and is abbreviated LAC in Table 1; valve type as endobronchial or intrabronchial; number of valves used in the treated lobe; and tissue-to-air volume ratio in the lower lobe of the treated lung, abbreviated TreatedLL_TAR in Table 1. A description of the calculation of low attenuation cluster slope can be found in Mishima M, Hirai T, Itoh H, Nakano Y, Sakai H, Muro S, Nishimura K, Oku Y, Chin K, Ohi M, Nakamura T, Bates J H, Alencar A M, Suki B (1999) Complexity of terminal airspace geometry assessed by lung computed tomography in normal subjects and patients with chronic obstructive pulmonary disease. Proc Natl Acad Sci USA 96(16):8829-8834, for example. The whole lung was used for the calculation of the percentage of peripheral vessel volume in this example, but more localized measurements of PPVV could be used, such as by including only the lobar or sub-lobar vessels in the calculation. The cutoff between peripheral and central lung and vessel areas, such as for use in calculating PPVV, may be determined in a variety of ways. In this example, one iteration of a morphological erosion was applied to the vascular segmentation mask of the entire airway tree. This erosion removed a layer of most distal vascular voxels, which were then defined as peripheral. Alternatively, all vessels which are situated in the periphery of the lung at a certain distance from the pleura, such as within 3 cm, may be classified as peripheral while the remainder may be classified as central. In still other embodiments, one may define vessels as peripheral if they are the last vessel generations. Other measures of vascular destruction due to emphysematous or other lung disease besides PPVV, such as peripheral and artery-specific vascular measures, may alternatively be used as they can provide complementary value to parenchymal density measures and improve the predictive abilities of the system.

TABLE 1

| Predictors | | P-value | Odds Ratio (95% CI) |
|---|---|---|---|
| FI | | <.0001 | per +5: 1.39 (1.20, 1.61) |
| PPVV | <0.53 vs. ≥0.53 | 0.007 | 2.87 (1.33, 6.18) |
| LAC | <−1.32 vs. ≥−1.32 | 0.058 | 1.97 (0.98, 3.96) |
| Valve type | EBV vs. IBV | 0.01 | 3.25 (1.32, 7.99) |
| Number of valves | 4-6 vs. 1-2 | 0.04 | 2.80 (1.02, 7.67) |
| TreatedLL_TAR | <0.125 vs. ≥0.125 | 0.048 | 2.25 (1.01, 5.03) |

There was a difference in the rate of successful treatment between subjects with intrabronchial valves (40.5%) compared to endobronchial valves (56.2%) which skewed the results. When patients treated with intrabronchial valves were excluded and only those treated with endobronchial valves were analyzed, the several predictors shown in Table 1 above became insignificant. These predictors were valve type, number of valves, and tissue-to-air volume ratio in the lower lobe of the treated lung. Fissure integrity(p<0.0001), low attenuation cluster slope (p=0.01), and peripheral vessel volume (p=0.02) were identified as the main predictors of successful lung volume reduction for endobronchial valves. The odds ratio for positive lung volume reduction increased by 1.47 times for every 5% increase in fissure integrity (CI=[1.25, 1.72]) by 2.68 times when low attenuation cluster slope was less than −1.32 (CI=[1.21, 5.92]), and by 2.72 times when the peripheral vessel volume was less than 0.53 (CI=[1.14, 6.50]). ROC curves (AUC) demonstrated the superiority of the full quantitative CT model using the three predictors (fissure integrity, low attenuation cluster slope, and peripheral vessel volume, with an AUC=0.80) as compared to a 1-predictor model using fissure integrity alone (AUC=0.75).

QCT has the potential to improve prediction of successful lung volume reduction using CT-measured surrogates for collateral ventilation and a new vascular index of disease distribution, percentage of peripheral vessel volume or PPVV, introducing an objective and more efficient approach to patient selection and treatment planning.

EXAMPLE 4

The Chartis Pulmonary Assessment System™ has a reported accuracy level of 75% in predicting patient response to valve-based lung volume reduction therapy, with the definition of success being a 350 cc reduction in volume of the treated lobe following the procedure. In this example, CT predictors of response to endobronchial valve lung reduction therapy identified in Example 3 above were retrospectively compared to the use of the Chartis Pulmonary Assessment System for selection of patients likely to have successful outcome from a valve-based lung volume reduction procedure.

Pre-operative CT scans of 146 subjects who underwent endobronchial valve LVR with EBV valves (Zephyr™ EBV; Pulmonx Inc.) following a unilateral complete occlusion protocol. CT scans had been obtained at a baseline and at 3 months following the procedure. The scans were analyzed retrospectively using dedicated lung Quantitative Imaging software (Apollo®, VIDA Diagnostics, Iowa). Volumes of treated lobes were measured on the baseline and follow-up CT scans of each subject. A lobar volume reduction greater than 350 cc was considered to be indicative of positive response to treatment. The quantitative CT measures identified above in Example 3 as correlating to a successful lung volume reduction procedure for endobronchial valve placement were measured in the subjects' scans. These were: fissure integrity, low attenuation clusters, and patient's percent peripheral vessel volume. We refer to the use of these three predictors as the "full quantitative CT model."

First, we analyzed the ROC of the full quantitative CT model versus a model using fissure integrity only, with fissure integrity determined using the CT images as described above, using the full dataset to predict successful lung volume reduction treatment. The ROC analysis conducted on the full dataset validated the superiority of the full quantitative CT model (AUC=0.80) over the model consisting of using FI alone (the univariate model) to determine likelihood of successful LVR response (AUC=0.75). At the operating point corresponding to FI≥90% in the univariate model, the sensitivity was 76.8% and specificity was 60.9%. For the full quantitative CT model, the same specificity was achieved as the univariate model, but with a sensitivity of 90.2%. Using the univariate model, a fissure integrity of 82.9% corresponded to a 50% probability of successful lung volume reduction. With the full QCT model, the same probability of successful lung volume reduction (50%) could be obtained with a range of FI values from 72.9% to 98.9%, depending on the other variables, that is the low attenuation clusters, and patient's percent peripheral vessel volume.

Next, a subset of the subjects (n=113) without Chartis data were used to train the quantitative CT-Bayes classifier to maximize successful lung volume reduction predictive score. The remaining subjects (n=33) for whom the data set included data from a Chartis Pulmonary Assessment System,™ were then used as testing datasets to evaluate the relative performance of the quantitative CT-Bayes classifier versus Chartis in selecting those likely to have a successful outcome from lung volume reduction therapy. Table 2, below, confirms that QCT-Bayes patient-selection method is superior to univariate quantitative CT module using fissure integrity alone and is comparable to the prediction of successful lung volume reduction using the Chartis Pulmonary Assessment System.™

TABLE 2

| Patient Selection Method | # Patients recommended for treatment | Responder Rate | Accuracy | Sensitivity | Specificity |
|---|---|---|---|---|---|
| Chartis | 57.6% (19/33) | 78.9% (15/19) | 78.8% (26/33) | 83.3% (15/18) | 73.3% (11/15) |
| QCT-Bayes | 63.6% (21/33) | 76.2% (16/21) | 78.8% (26/33) | 88.9% (16/18) | 66.7% (10/15) |
| QCT-FI≥90% | 57.6% (19/33) | 73.7% (14/19) | 72.7% (24/33) | 77.8% (14/18) | 66.7% (10/15) |

EXAMPLE 5

Bronchoscopy-guided lung volume reduction treatment with coils is a new procedure targeting the treatment of patients with severe emphysema. It has been shown to be effective in treating both homogeneous and heterogeneous emphysema patients, with and without indicators of collateral ventilation. The purpose of this Example is to identify pre-operative Computed Tomography (CT) quantitative measurements associated with positive treatment outcome.

Computed tomography scans from 22 subjects with severe emphysema patients were acquired at full inspiration prior to the procedure. Lung volume reduction coils (PneumRx, Mountain View, Calif.) were then implanted to one targeted lobe using fluoroscopic guidance. Clinical data including FEV1, residual volume (RV) and 6-minute walk distance (6MWD) were collected prior to the procedure and at 3 months after treatment. Changes in these clinical data were used as indicators of the treatment efficacy. Quantitative CT measurements were determined from the pre-operative scans using dedicated lung quantitative imaging software Apollo® (VIDA Diagnostics, Coralville, Iowa). These measurements were for the targeted lobe and included: fissure integrity; emphysema percentage, abbreviated EP, which was defined as percentage of low attenuation areas below a threshold of −950 HU; and heterogeneity score, abbreviated HS, which was defined as the difference between percentage between the treated lobe and the non-treated ipsilateral lobe or the weighted average of the ipsilateral non-treated lobes. In addition, the emphysema severity and subtype was determined in the targeted lobe by performing low attenuation cluster (LAC) based measurements (slope, hole size mean (HSM) which is the mean volume of a low attenuation cluster (contiguous voxels of below a threshold of −950 HU), and hole size standard deviation (HSSD) which is the standard deviation of the size of the low attenuation clusters). A threshold of −950 Hounsfield Unit (HU) was used in the analysis as a CT indicator of emphysema. Spearman correlations between efficacy measurements and CT derived quantitative measurements were evaluated.

Among the subjects, 68.2% (15/22) experienced a large improvement in exercise capacity with a change in 6 minute walking distance of greater than or equal to 26 meters. The difference in emphysema percentage between those identified as having a successful procedure result as compared to those EP difference was shown to be significant (p=0.04) but the significant difference was observed for fissure integrity (p=0.19) or HS (p=0.95). As shown in Table 3, below, HS and FI had a weak or no correlation against all efficacy measurements, which suggests that inter-lobar collateral ventilation and emphysema heterogeneity across the treated lung may not play important roles in coil-based lung volume reduction procedures. However, significant correlations were observed for the following intra-lobar quantitative CT measurements: EP vs. Δ6MWD ($\rho$=0.59), EP vs. ΔRV ($\rho$=−0.72), LAC-HSM vs. ΔRV ($\rho$=−0.63), LAC-HSM vs. Δ6MWD ($\rho$=−0.49), LAC-HSSD vs. ΔRV ($\rho$=−0.69), and LAC-HSSD vs. Δ6MWD ($\rho$=−0.56). No significant correlation was observed between ΔFEV1 and quantitative measurements.

TABLE 3

|  | ΔFEV1 | ΔRV | Δ6MWD |
|---|---|---|---|
| FI | −0.043 (0.85) | 0.13 (0.56) | 0.17 (0.46) |
| EP | 0.29 (0.19) | −0.72 (<0.001) | 0.59 (<0.01) |
| HS | −0.027 (0.91) | −0.30 (0.17) | 0.06 (0.79) |
| LAC-Slope | 0.18 (0.41) | −0.44 (<0.05) | 0.26 (0.24) |
| LAC-HSM | 0.19 (0.39) | −0.63 (<0.01) | 0.49 (<0.05) |
| LAC-HSSD | 0.2 (0.37) | −0.69 (<0.001) | 0.56 (<0.01) |

These results suggest that quantitative CT measurements characterizing emphysema magnitude, distribution and severity within the treated lobe are associated with the efficacy of lung volume reduction coil procedures. These quantitative CT measurements may therefore be used as predictors for improved patient selection to achieve a greater treatment response.

EXAMPLE 6

In this example, 385 CT scans were analyzed using dedicated quantitative CT lung software as described herein. The subjects of the scans were current and former smokers, both with and without lung disease. The analysis included QCT measurements of density, airway measurements, vessel measurements, functional measurements, and nodule dimensions and characteristics.

Demographic information was available for 380 of the 385 subjects. Of these, 311 were 55 years old or older, 228 had a 30 or more pack-year history of smoking, 344 had less than 15 years since quitting smoking, and 120 had proven lung cancer by biopsy or imaging. There were equal numbers of women and men.

The analysis showed that air trapping and airway thickness were both strongly associated with lung cancer, with each having a p<0.01. Parenchymal measurements including low attenuation clusters representative of disease severity (p=0.01) and a centrilobular pattern of emphysema as assessed by visual experts (p=0.04) were also associated with lung cancer but less strongly than the airway disease related QCT metrics.

These results show that QCT measurement can be used to predict increased risk of lung cancer and can be applied to a system for recommending lung cancer screening. The prediction of lung cancer risk can be improved through the use of functional airway and emphysema measurements as well as QCT measurements of longitudinal differences.

In the foregoing detailed description, the invention has been described with reference to specific embodiments. However, it may be appreciated that various modifications and changes can be made without departing from the scope of the invention.

The invention claimed is:

1. A system for predicting an outcome of a lung volume reduction procedure for a patient comprising:
   a user interface;
   a processor;
   programing operable on the processor for predicting an outcome of the bronchoscopic lung volume reduction procedure;
   wherein predicting the outcome of the lung volume reduction procedure comprises:
   receiving patient data comprising volumetric images of the patient;
   analyzing the volumetric images to identify one or more features correlated to treatment outcome prediction;
   predicting an outcome for a treatment modality or treatment device using the one or more identified features; and
   generating text and/or imagery describing the predicted outcome.

2. The system of claim 1 further comprising receiving a selected treatment location within the airway tree from a user and predicting an outcome for a treatment modality or treatment device at the selected location using the one or more identified features.

3. The system of claim 1 wherein generating text and/or imagery describing the predicted outcome of the lung volume reduction procedure further comprises receiving a selected treatment modality from the user, and wherein predicting an outcome for a treatment modality comprises predicting an outcome for the treatment modality selected by the user.

4. The system of claim 1 wherein predicting an outcome for a treatment modality comprises predicting a plurality of outcomes for a plurality of treatment modalities, and wherein generating text and/or imagery describing the predicted outcome comprises generating text and/or imagery describing the plurality of treatment outcomes for the plurality of treatment modalities.

5. The system of claim 1 further comprising programming operable on the processor for analyzing the volumetric images to identify lobes, sublobes and an airway tree of the lungs and generating a three dimensional model of the patient's lungs.

6. The system of claim 1 wherein the predicted outcome comprises a numerical value representing a probability of success.

7. The system of claim 6 wherein success comprises a lung volume reduction greater than a threshold value.

8. The system of claim 1 wherein the predicted outcome comprises a numerical value representing a probability of pneumothorax.

9. The system of claim 1 wherein the predicted outcome comprises a first numerical value representing a probability of lung volume reduction greater than a threshold value and a second numerical value representing a probability of pneumothorax.

10. The system of claim 1 wherein the one or more features includes a feature corresponding to fissure integrity.

11. The system of claim 1 wherein analyzing the volumetric images to identify one or more features correlated to treatment outcome prediction comprises measuring low attenuation clusters.

12. The system of claim 1 wherein analyzing the volumetric images to identify one or more features correlated to treatment outcome prediction comprises measuring peripheral vessel volume.

13. A system for predicting an outcome of a lung volume reduction procedure for a patient comprising:
    a user interface;
    a processor;
    programming operable on the processor for predicting an outcome of the bronchoscopic lung volume reduction procedure on a user interface;
    wherein predicting the outcome of the lung volume reduction procedure comprises:
    receiving patient data comprising volumetric images of the patient;
    analyzing the volumetric images to identify lobes and airway tree of the lungs;
    analyzing the volumetric images to identify one or more features correlated to treatment outcome prediction;
    generating a three dimensional model of the patient's lungs;
    receiving a selected treatment location within the airway tree from a user;
    predicting an outcome for a treatment modality or treatment device at the selected location using the one or more identified features; and
    generating text and/or imagery describing the predicted outcome.

14. The system of claim 13 wherein generating text and/or imagery describing the predicted outcome of the lung volume reduction procedure further comprises receiving a selected treatment modality or treatment device from the user, and wherein predicting an outcome for a treatment modality comprises predicting an outcome for the treatment modality or treatment device selected by the user.

15. The system of claim 13 wherein predicting an outcome for a treatment modality or treatment device comprises predicting a plurality of outcomes for a plurality of treatment modalities or treatment devices, and wherein generating text and/or imagery describing the predicted outcome on the user interface comprises generating text and/or imagery describing the plurality of treatment outcomes for the plurality of treatment modalities on the user interface.

16. The system of claim 13 wherein the predicted outcome comprises a numerical value representing a probability.

17. The system of claim 16 wherein the predicted outcome comprises a probability of success.

18. The system of claim 13 wherein predicting an outcome for the selected treatment modality using one or more identified features comprises comparing the one or more features identified in the patient lungs to a database to predict an outcome of treatment at the selected location with the selected treatment modality.

19. The system of claim 18 wherein the database comprises a set of outcomes for lung volume reduction procedures for a group of individuals using the selected treatment modality and further comprises a set of volumetric images or one or more features identified in the volumetric images for the group of individuals, wherein the identified features in the volumetric images of the group of individuals are the same features as the identified features in the volumetric images of the patient.

20. The system of claim 13 wherein generating text and/or imagery describing the predicted outcome of the lung volume reduction procedure further comprises generating text and/or imagery describing a probability of a successful treatment outcome and a probability of an adverse event for a plurality of lung volume reduction treatment modalities and receiving a selection of a treatment modality from a user.

* * * * *